US011591362B2

(12) United States Patent
Bleicher et al.

(10) Patent No.: US 11,591,362 B2
(45) Date of Patent: Feb. 28, 2023

(54) ORTHOGONAL PROTECTING GROUPS FOR THE PREPARATION OF STEREODEFINED PHOSPHOROTHIOATE OLIGONUCLEOTIDES

(71) Applicant: Roche Innovation Center Copenhagen A/S, Hørsholm (DK)

(72) Inventors: Konrad Bleicher, Basel (CH); Dennis Jul Hansen, Hørsholm (DK); Erik Daa Funder, Hørsholm (DK)

(73) Assignee: Roche Innovation Center Copenhagen A/S, Horsholm (DK)

( * ) Notice: Subject to any disclaimer, the term of this patent is extended or adjusted under 35 U.S.C. 154(b) by 0 days.

(21) Appl. No.: 16/497,952

(22) PCT Filed: Mar. 20, 2018

(86) PCT No.: PCT/EP2018/057069
§ 371 (c)(1),
(2) Date: Sep. 26, 2019

(87) PCT Pub. No.: WO2018/177825
PCT Pub. Date: Oct. 4, 2018

(65) Prior Publication Data
US 2021/0179658 A1 Jun. 17, 2021

(30) Foreign Application Priority Data
Mar. 29, 2017 (EP) .................................... 17163506

(51) Int. Cl.
*C07H 21/04* (2006.01)
*C07H 1/00* (2006.01)
*C07H 19/10* (2006.01)

(52) U.S. Cl.
CPC ............... *C07H 21/04* (2013.01); *C07H 1/00* (2013.01); *C07H 19/10* (2013.01)

(58) Field of Classification Search
CPC .......... C07H 21/04; C07H 21/02; C07H 1/00; C07H 19/10
See application file for complete search history.

(56) References Cited

U.S. PATENT DOCUMENTS

| 7,186,822 | B2 | 3/2007 | Ravikumar et al. |
| 2011/0294124 | A1 | 12/2011 | Wada et al. |
| 2012/0316224 | A1 | 12/2012 | Verdine et al. |
| 2015/0211006 | A1 | 7/2015 | Butler et al. |

FOREIGN PATENT DOCUMENTS

| CN | 102282155 A | 12/2011 |
| CN | 102596204 A | 7/2012 |
| CN | 104661664 A | 5/2015 |
| EP | 1984381 | 10/2008 |
| EP | 2620428 | 7/2013 |
| JP | 2015-528002 A | 9/2015 |
| WO | 01/88198 A1 | 11/2001 |
| WO | WO2007/090071 | 8/2007 |
| WO | WO2007/112754 | 10/2007 |
| WO | WO 2005/092909 | 2/2008 |
| WO | WO2009/043353 | 4/2009 |
| WO | WO2009/124238 | 10/2009 |
| WO | WO2010/036698 | 1/2010 |
| WO | WO 2011/005761 | 1/2011 |
| WO | WO 2017/157672 | 9/2017 |
| WO | WO 2017/194498 | 11/2017 |
| WO | WO 2017/198775 | 11/2017 |

OTHER PUBLICATIONS

Wuts et al., ed., Greene's Protective Groups in Organic Synthesis, John Wiley & Sons Inc., 4th ed., 2007, p. 696-926. (Year: 2007).*
Kaur et al., Chem. Rev., 2007, 107, p. 4672-4697. (Year: 2007).*
Bergstrom "Unnatural Nucleosides with Unusual Base Pairing Properties," Current Protocols in Nucleic Acid Chemistry, Jun. 1, 2009, 37(1):1.4.1.-1.4.32.
Capaldi and Scozzari, "Manufacturing and Analytical Processes for 2'-O-(2-Methoxyethyl)-Modified Oligonucleotides," Antisense Drug Technology: Principles, Strategies, and Applications, CRC Press, 2008, Chapter 14, pp. 401-434.
Hirao et al., "Natural versus artificial creation of base pairs in DNA: origin of nucleobases from the perspectives of unnatural base pair studies," Accounts of Chemical Research, Dec. 18, 2012, 45(12):2055-2065.
International Search Report and Written Opinion in International Application No. PCT/EP2018/057069, dated Jun. 22, 2018, 11 pages.
Oka et al., "Solid-phase synthesis of stereoregular oligodeoxyribonucleoside phosphorothioates using bicyclic oxazaphospholidine derivatives as monomer units," J Am Chem Soc., Nov. 26, 2008, 130(47):16031-16037.
Oka et al., "Diastereocontrolled synthesis of dinucleoside phosphorothioates using a novel class of activators, dialkyl(cyanomethyl)ammonium tetrafluoroborates," J Am Chem Soc., May 8, 2002, 124(18):4962-4963.
Ravikumar et al.,"UnyLinker: An Efficient and Scaleable Synthesis of Oligonucleotides Utilizing a Universal Linker Molecule: A Novel Approach To Enhance the Purity of Drugs," Org Process Res Dev., 2008, 12(3):399-410.
Seth at al., "Synthesis and biophysical evaluation of 2',4'-constrained 2'O-methoxyethyl and 2',4'-constrained 2'O-ethyl nucleic acid analogues," J Org Chem., Mar. 5, 2010, 75(5):1569-1581.
International Preliminary Report on Patentability in International Application No. PCT/EP2018/057069, dated Oct. 1, 2019, 8 pages.
Office Action received for Chinese Patent Application No. 201880022722.3, dated Sep. 23, 2022, 22 pages (10 pages of English Translation and 12 pages of Original Document).

(Continued)

*Primary Examiner* — Jonathan S Lau
(74) *Attorney, Agent, or Firm* — Smith Gambrell & Russell LLP; Judy Jarecki-Black; Ram W. Sabnis

(57) ABSTRACT

The present invention relates to the field of stereodefined phosphorothioate oligonucleotides and to stereodefining nucleoside monomers comprising an amine containing chiral auxiliary group, and methods of orthogonally protecting the nitrogen of chiral auxiliaries during oligonucleotide synthesis, preventing post elongation chain cleavage, increasing yield and purity of stereodefined phosphorothioate oligonucleotides.

39 Claims, 4 Drawing Sheets

(56) References Cited

OTHER PUBLICATIONS

Figure 1:
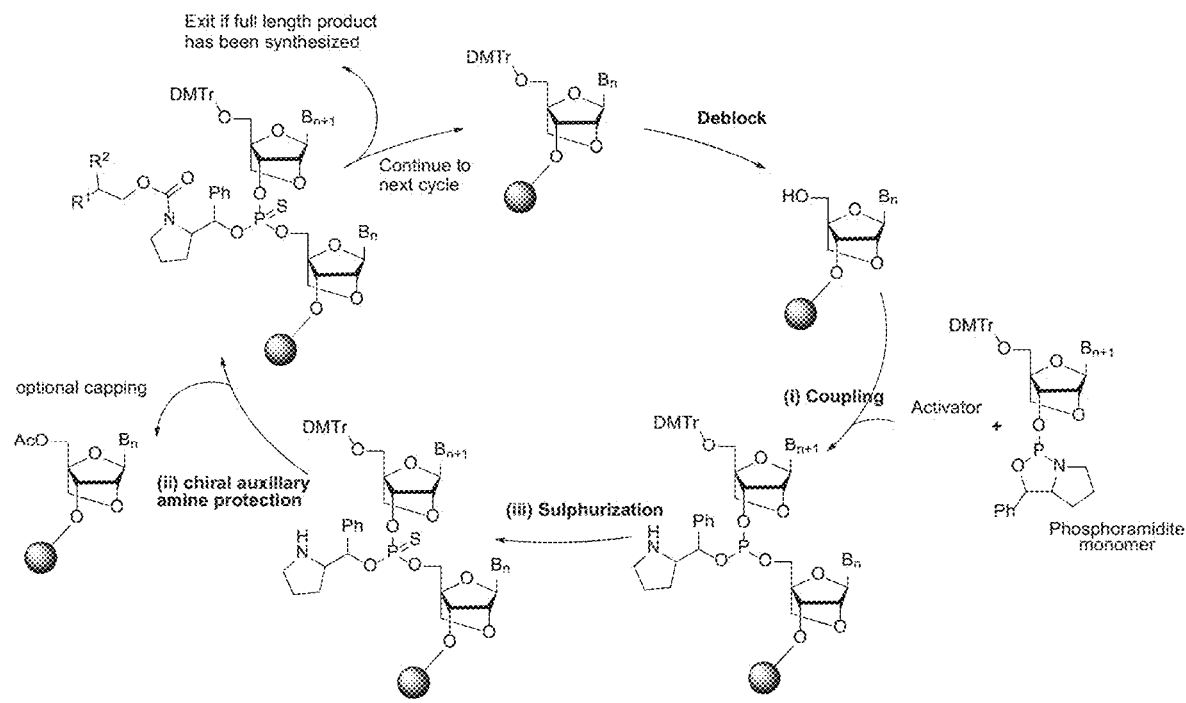

Office Action received for European Application No. 18715527.0, dated May 16, 2022, 4 pages.
"Protection for the Amino Group", Protective Groups in Organic Synthesis, Fifth Edition, 895-899 (2014).
"Protection for the Amino Group", Protective Groups in Organic Synthesis, Fifth Edition, 907-921 (2014).
Notice for Reasons for Rejection issued for JP 2019-553219 dated Mar. 16, 2022 (3 pages of English Translation, 3 pages of Original Document).
Oka, N., et al., "Solid-Phase Synthesis of Stereoregular Oligodeoxyribonucleoside Phosphorothioates Using Bicyclic Oxazaphospholidine Derivatives as Monomer Units", Journal of the American Chemical Society, 130(47): 16031-16037 (2008).

\* cited by examiner

ORTHOGONAL PROTECTING GROUPS FOR THE PREPARATION OF STEREODEFINED PHOSPHOROTHIOATE OLIGONUCLEOTIDES

FIELD OF THE INVENTION

The present invention relates to the field of stereodefined phosphorothioate oligonucleotides and to stereodefining nucleoside monomers comprising an amine containing chiral auxiliary group, and methods of orthogonally protecting the nitrogen of chiral auxiliaries during oligonucleotide synthesis, preventing post elongation chain cleavage, increasing yield and purity of stereodefined phosphorothioate oligonucleotides. The orthogonal protection groups are also rapidly removed, typically within 4 hours.

BACKGROUND TO THE INVENTION

The use of stereodefined phosphorothioate internucleoside linkages in oligonucleotides allow for the optimisation of the pharmacological profile of therapeutic oligonucleotides. However, the manufacture of stereodefined phosphorothioate oligonucleotides is at present comparatively inefficient as compared to non stereodefined phosphorothioate oligonucleotides. There is therefore a need to improve the efficiency of synthesis of stereodefined oligonucleotides.

Oka et al., J. AM. CHEM. SOC. 2008, 130, 16031-16037, reports on the solid phase synthesis of stereoregular DNA phosphorothioates using bicyclic oxazaphospholidine derivatives. In the Oka et al. process, the amine on the oxazaphospholidine chiral auxiliary is protected by trifluroacetylation.

EP 2 620 428A1 paragraph [0015] reports that the removal of the trifluoroacetyl group causes problems in the synthesis of long DNA strands or chemically unstable RNA strands, possibly due to decomposition of the strand or problems in complete removal of the group. EP 2 620 428A1 proposes the use of a different chiral auxiliary.

The present invention is based on the finding that the Oka et al., method results in significant premature chain termination, and that the use of a carbamate protection group rather than a triflouroacetyl protection group on the amine of the oxazaphospholidine chiral auxiliary allows for rapid and efficient deprotection and cleavage of the chiral auxiliary whilst avoiding premature chain termination.

STATEMENT OF INVENTION

The invention provides for a method for the synthesis of a stereodefined phosphorothioate oligonucleotide, said method comprising the steps of (i) coupling oxazaphospholidine chiral auxiliary phosphoramidite monomer to the 5'-OH group of a nucleoside, followed by the step (ii) of protecting the amine group of the oxazaphospholidine chiral auxiliary with a carbamate protection group, and (iii) sulfurization, wherein the sulfurization step (iii) is performed after the coupling step (i) and either prior to or subsequent to the amine protection step (ii).

The invention provides for a method for the synthesis of a stereodefined phosphorothioate oligonucleotide, said method comprising the steps of (i) coupling a oxazaphospholidine chiral auxiliary phosphoramidite monomer to the 5'-OH group of a nucleoside to produce a phosphite triester intermediate, followed by the step (ii) of protecting the amine group of the oxazaphospholidine chiral auxiliary with a carbamate protection group, and (iii) oxidising the phosphite triester intermediate with a sulfurizing reagent, wherein the sulfurization step (iii) is performed after the coupling step (i) and either prior to or subsequent to the amine protection step (ii).

The invention provides for a method for the synthesis of a stereodefined phosphorothioate oligonucleotide, said method comprising the steps of (i) coupling a oxazaphospholidine chiral auxiliary phosphoramidite monomer to the 5'-OH group of a nucleoside bound to a solid support, to produce a phosphite triester intermediate, followed by the step (ii) of protecting the amine group of the oxazaphospholidine chiral auxiliary with a carbamate protection group, and (iii) oxidising the phosphite triester intermediate with a sulfurizing reagent, wherein the sulfurization step (iii) is performed after the coupling step (i) and either prior to or subsequent to the amine protection step (ii), followed by removal of the carbamate protection group and cleavage of the oligonucleotide from the solid support.

The invention provides for, the use of a carbamate protection group, such as an orthogonal carbamate protection group, on a chiral auxiliary group to prevent strand cleavage of an oligonucleotide during synthesis of a stereodefined phosphorothioate oligonucleotide. The strand cleavage prevented may be strand cleavage at the phosphate triester.

The invention provides for, a compound of formula 21 or 22

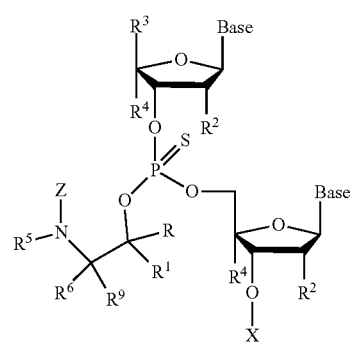

Formula 21

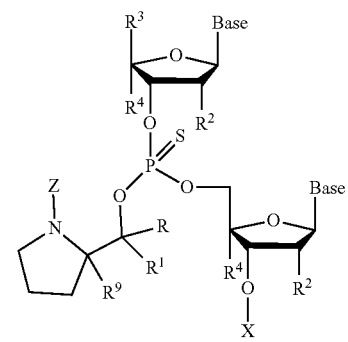

Formula 22 wherein X is either a solid support or a preceding nucleoside attached to the solid support (a terminal 5'-OH group);
Base is a nucleobase;
$R^5$ and $R^6$ are independently selected from the group consisting of hydrogen, alkyl, cyclo-alkyl, aryl, heteroaryl, substituted alkyl, substituted cyclo-alkyl, substituted aryl, and substituted heteroaryl, or $R^5$ and $R^6$ together form a heterocyclic ring comprising 3-16 carbon atoms, together with the N atom of formula (I);
$R^1$ is selected from the groups consisting of hydrogen and $C_1$-3 alkyl; $R^9$ is hydrogen; R is selected from the groups consisting of aryl, heteroaryl, substituted aryl, substituted heteroaryl, nitro, halogen, cyano, silyl, substituted silyl, sulfone, substituted sulfone (aryl substituted sulfone), fluorene, and substituted fluorine;

$R^3$= is selected from the group consisting of $CH_2ODMTr$, $CH_2$-Alkyl-O-DMTr, CH-Me-O-DMTr, $CH_2OMMTr$, $CH_2$-Alkyl-O-MMTr, CH(Me)-O-MMTr, CH—$R^a$—O-DMTr$R^b$, and CH—$R^a$—O-MMTr$R^b$;

$R^2$ is selected from the groups consisting of halo, such as —F, amino, azido, —SH, —CN, —OCN, —$CF_3$, —$OCF_3$, —O($R_m$)-alkyl, —S($R_m$)-alkyl, —N($R_m$)-alkyl, —O($R_m$)-alkenyl, —S($R_m$)-alkenyl, —N($R_m$)-alkenyl; —O($R_m$)-alkynyl, —S($R_m$)-alkynyl or —N($R_m$)-alkynyl; O-alkylenyl-O-alkyl, alkynyl, alkaryl, aralkyl, O-alkaryl, O-aralkyl, $O(CH_2)_2SCH_3$, O—$(CH_2)_2$—O—N($R_m$)($R_n$) or O—$CH_2$C(=O)—N($R_m$)($R_n$), —O—$(CH_2)_2OCH_3$, and —O—$CH_3$, where each $R_m$ and $R_n$ are independently, H, an amino protecting group or substituted or unsubstituted $C_{1-10}$ alkyl;

$R^4$= is selected from the group consisting of alkyl, cyclo-alkyl, cyclo-heteroalkyl, O-alkyl, S-alkyl, NH-alkyl, and hydrogen;

or $R^2$ and $R^4$ together designate a bivalent bridge consisting of 1, 2, 3 groups/atoms selected from the group consisting of —C($R^aR^b$)—, —C($R^a$)=C($R^b$), —C($R^a$)=N, O, —Si($R^a$)$_2$—, S—, —$SO_2$—, —N($R^a$)—, and >C=Z;

wherein $R^a$ and, when present $R^b$, each is independently selected from hydrogen, optionally substituted $C_{1-6}$-alkyl, optionally substituted $C_{2-6}$-alkenyl, optionally substituted $C_{2-6}$-alkynyl, hydroxy, optionally substituted $C_{1-6}$-alkoxy, $C_{2-6}$-alkoxyalkyl, $C_{2-6}$-alkenyloxy, carboxy, $C_{1-6}$-alkoxycarbonyl, $C_{1-6}$-alkylcarbonyl, formyl, aryl, aryloxy-carbonyl, aryloxy, arylcarbonyl, heteroaryl, hetero¬aryloxy-carbonyl, heteroaryloxy, heteroarylcarbonyl, amino, mono- and di($C_{1-6}$-alkyl)amino, carbamoyl, mono- and di($C_{1-6}$-alkyl)-aminocarbonyl, amino-$C_{1-6}$-alkyl-aminocarbonyl, mono- and di($C_{1-6}$-alkylamino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkyl-thio, halogen, where aryl and heteroaryl may be optionally substituted and where two geminal substituents Ra and Rb together may designate optionally substituted methylene (=$CH_2$), wherein for all chiral centers, asymmetric groups may be found in either R or S orientation; and Z is a carbamate protection group.

FIGURES

FIG. 1: Illustrative oligonucleotide synthesis cycles of the invention. Note that the nucleosides illustrated are beta-D-oxy-LNA, however other nucleosides as detailed herein may be used. The figure illustrates the process where step (i), (iii) and then (ii) are performed sequentially, and optionally, after step (ii) a capping step may be performed.

Figure 2:
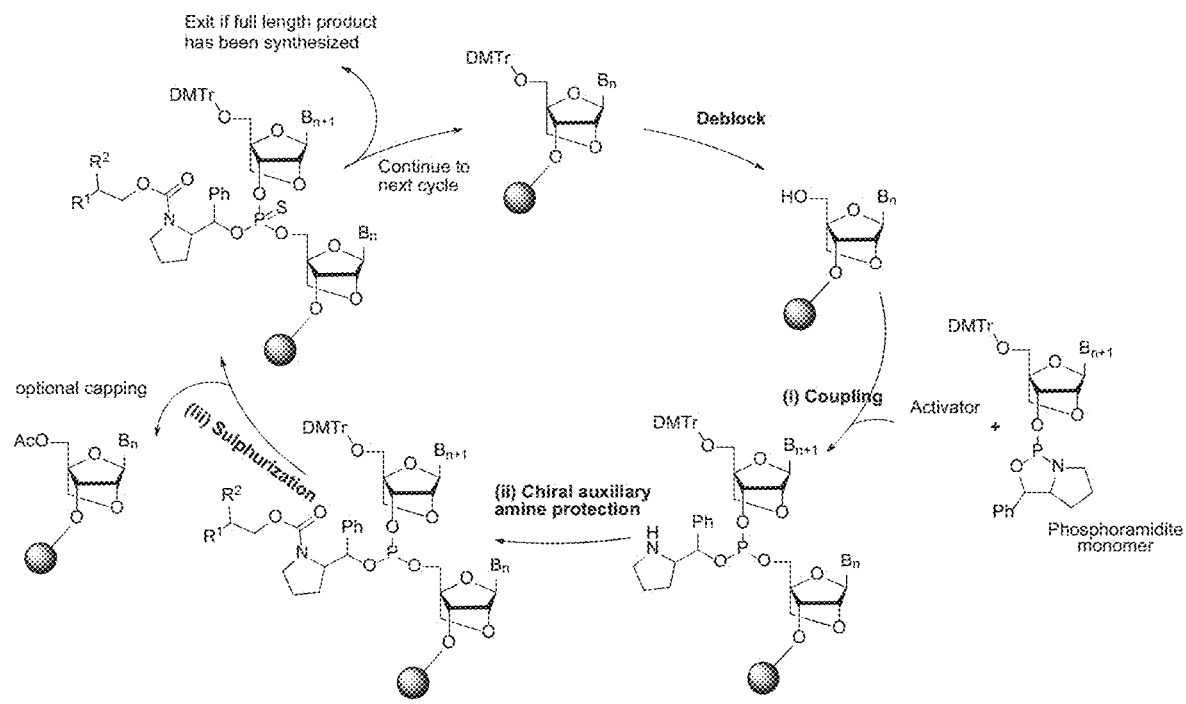

FIG. 2: Illustrative oligonucleotide synthesis cycles of the invention. Note that the nucleosides illustrated are beta-D-oxy-LNA, however other nucleosides as detailed herein may be used. The figure illustrates the process where step (i), (ii) and then (iii) are performed sequentially, and optionally, after step (iii) a capping step may be performed.

Figure 3:
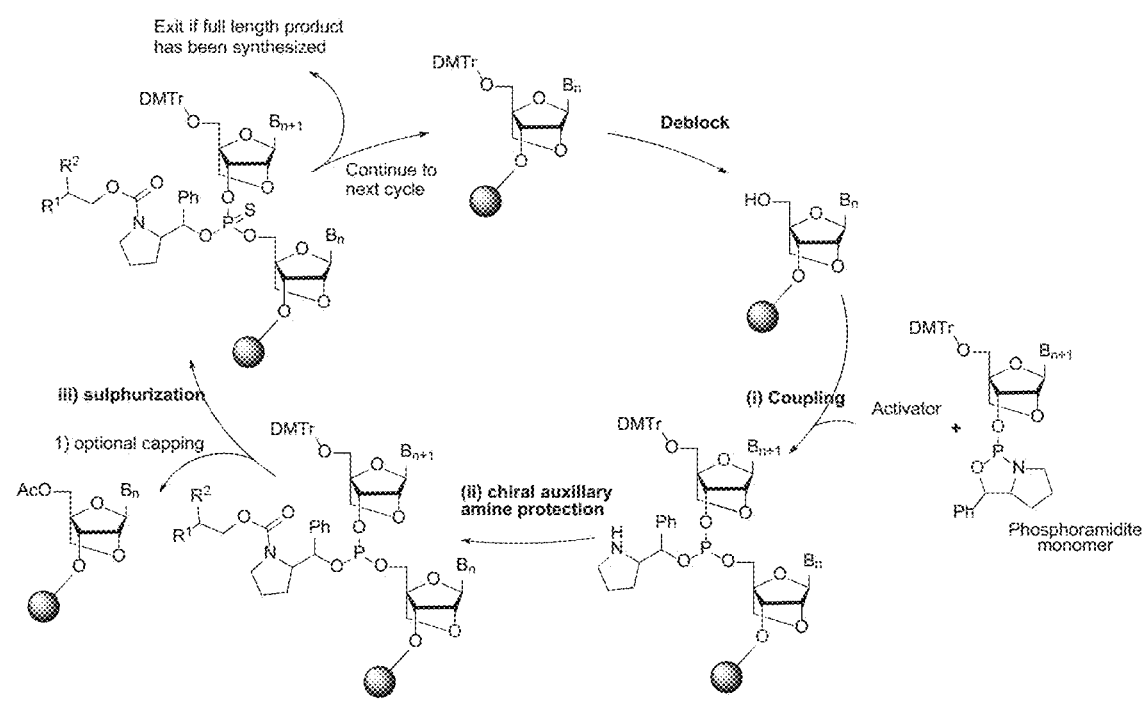

FIG. 3: Illustrative oligonucleotide synthesis cycles of the invention. Note that the nucleosides illustrated are beta-D-oxy-LNA, however other nucleosides as detailed herein may be used. The figure illustrates the process where step (i), (ii) and then (iii) are performed sequentially, and optionally, after step (ii) and prior to step (iii) a capping step may be performed.

Figure 4:
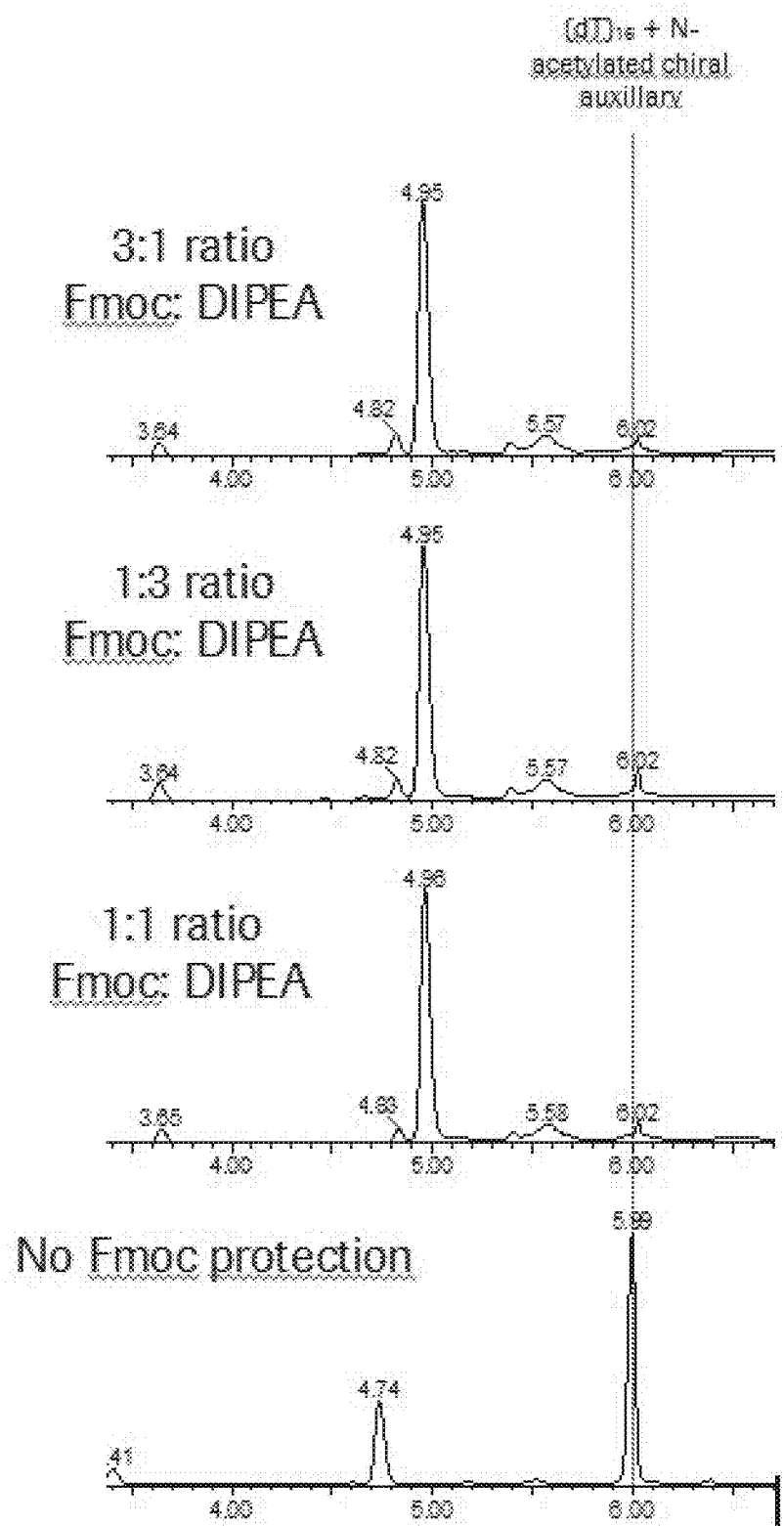

FIG. 4: Chromatograms showing that when Fmoc protection is carried out before capping, a very rapid deprotection of the chiral auxiliary is observed, compared to when no Fmoc protection is carried out.

Figure 5:
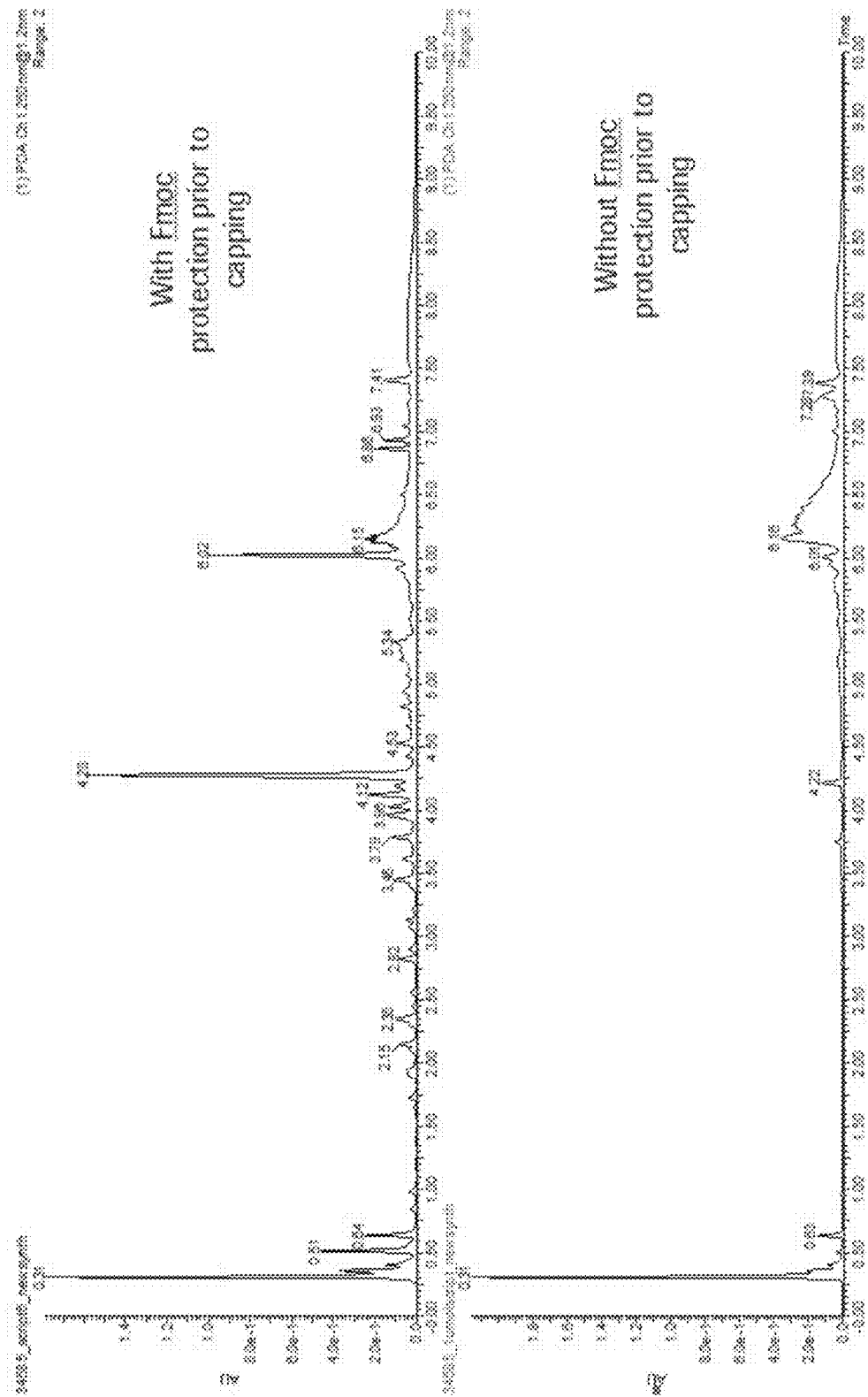

FIG. 5: Chromatogram of a fully stereodefined oligonucleotide synthesised according to the synthesis cycle of FIG. 1, compared to the equivalent without Fmoc protection, analysed after 4 hours deprotection, indicating that rapid deprotection is observed only when Fmoc protection is carried out.

DETAILED DESCRIPTION

As used herein, the term "aryl" refers to an aromatic ring wherein each of the atoms forming the ring is a carbon atom. Aryl rings are formed by five, six, seven, eight, nine, or more than nine carbon atoms. Aryl groups are a substituted or unsubstituted. In one aspect, an aryl is a phenyl or a naphthalenyl. Depending on the structure, an aryl group can be a monoradical or a diradical (i.e., an arylene group). In one aspect, an aryl is a $C_{6-10}$ aryl. In some embodiments aryl is phenyl. When substituted aryl may be substituted with a group selected from the group consisting of: $C_{1-4}$ alkyl group, $C_{6-14}$ aryl group $C_{1-4}$, alkoxy group, $C_{7-14}$ aralkyl group, $C_{1-4}$ alkyl, $C_{6-14}$ aryl group, $C_{1-4}$ alkoxy, $C_{6-14}$ aryl group, or $C_{6-14}$ aryl $C_{1-4}$ alkyl group. Multiple substitutions may be dependently or independently selected from the group consisting of: $C_{1-4}$ alkyl group, $C_{6-14}$ aryl group $C_{1-4}$, alkoxy group, $C_{7-14}$ aralkyl group, $C_{1-4}$ alkyl, $C_{6-14}$ aryl group, $C_{1-4}$ alkoxy, $C_{6-14}$ aryl group, or $C_{6-14}$ aryl $C_{1-4}$ alkyl group; or a group selected from the group consisting of halide, such as iodide, fluoride, bromide or chloride, such as phenyl substituted with halide, such as iodide, fluoride, bromide or chloride.

An "alkyl" group refers to an aliphatic hydrocarbon group. The alkyl moiety may be a saturated alkyl group (which means that it does not contain any units of unsaturation, e.g. carbon-carbon double bonds or carbon-carbon triple bonds) or the alkyl moiety may be an unsaturated alkyl group (which means that it contains at least one unit of unsaturation). The alkyl moiety, whether saturated or unsaturated, may be branched, straight chain, or include a cyclic portion. The point of attachment of an alkyl is at a carbon atom that is not part of a ring. The "alkyl" moiety may have 1 to 10 carbon atoms (whenever it appears herein, a numerical range such as "1 to 10" refers to each integer in the given range; e.g., "1 to 10 carbon atoms" means that the alkyl group may consist of 1 carbon atom, 2 carbon atoms, 3 carbon atoms, etc., up to and including 10 carbon atoms, although the present definition also covers the occurrence of the term "alkyl" where no numerical range is designated). Alkyl includes both branched and straight chain alkyl groups. The alkyl group of the compounds described herein may be designated as "$C_{1-6}$ alkyl" or similar designations. By way of example only, "$C_{1-6}$ alkyl" indicates that there are one, two, three, four, five, or six carbon atoms in the alkyl chain, i.e., the alkyl chain is selected from the group consisting of methyl, ethyl, propyl, iso-propyl, n-butyl, isobutyl, sec-butyl, and tert-butyl. Typical alkyl groups include, but are in no way limited to, methyl, ethyl, propyl, isopropyl, butyl, isobutyl, tertiary butyl, pentyl, hexyl, allyl, cyclopropylmethyl, cyclobutylmethyl, cyclopentylmethyl, cyclohexylmethyl, and the like. In one aspect, an alkyl is a $C_{1-6}$ or $C_{1-4}$ alkyl or $C_{1-3}$ alkyl. $C_{1-3}$ alkyl group means straight or branched alkyl group that has 1 to 3 carbon atoms. Examples of $C_{1-4}$ alkyl group are methyl, ethyl, propyl and isopropyl. $C_{1-3}$ alkyl group means straight or branched alkyl group that has 1 to 4 carbon atoms. Examples of $C_{1-3}$ alkyl groups are methyl, ethyl, propyl, isopropyl, butyl, isobutyl, and tert-butyl.

"Alkenyl" groups are straight chain, branch chain, and cyclic hydrocarbon groups containing at least one carbon-carbon double bond. Alkenyl groups can be substituted. "Alkynyl" groups are straight chain, branch chain, and cyclic hydrocarbon groups containing at least one carbon-carbon triple bond. Alkynyl groups can be substituted. An "alkoxy" group refers to an alklyl group linked to oxygen i.e. (alkyl)-O— group, where alkyl is as defined herein. Examples include methoxy (—$OCH_3$) or ethoxy (—$OCH_2CH_3$) groups.

An "alkenyloxy" group refers to an alkenyl group linked to oxygen i.e. (alkenyl)-O— group, where alkenyl is as defined herein.

An "alkynyloxy" group refers to an alkynyl group linked to oxygen i.e. (alkynyl)-O— group, where alkynyl is as defined herein.

An "aryloxy" group refers to an aryl group linked to oxygen i.e. (aryl)-O— group, where the aryl is as defined herein. An example includes phenoxy (—$OC_6H_5$) group.

"Silyl" refers to $H_3Si$—. "Substituted silyl" as used herein, refers to a moiety which has one or more the hydrogen of silyl substituted. Examples include, but are not limited to, TBDMS (tert-butyldimethylsilyl), TBDPS (tert-butyldiphenylsilyl) or TMS (trimethylsilyl) group.

The term "halogen" is intended to include fluorine, chlorine, bromine and iodine. The term "halide" includes fluoride, bromide, iodide and chloride.

An "acyl protection group" comprises an acyl group —C(=O)—$R^7$, wherein $R^7$ is a terminal group, for example a group selected from, alkyl-, alkyl-, alkenyl-, alkynyl-, cycloalkyl- and aryl-group; or a group selected from, unsubstituted alkyl-, unsubstituted alkenyl-, unsubstituted alkynyl-, unsubstituted cycloalkyl- or unsubstituted aryl-group; or a group selected from substituted alkyl-, substituted alkenyl-, substituted alkynyl-, substituted cycloalkyl- or substituted aryl-group. In some embodiments $R^7$ may be selected from the group consisting of unsubstituted $C_{1-6}$-alkyl-, unsubstituted $C_{2-6}$-alkenyl-, unsubstituted $C_{2-6}$-alkinyl-, unsubstituted $C_{3-7}$-cycloalkyl- or unsubstituted phenyl-group or substituted $C_{1-6}$-alkyl-, substituted $C_{2-6}$-alkenyl-, substituted $C_{2-6}$-alkinyl-, substituted $C_{3-7}$-cycloalkyl- or substituted phenyl-group; wherein when substituted, the substituent group may be mono or poly substituted, e.g. with one or more substituents selected from the group consisting of halogen, $C_{1-6}$-alkyl, $C_{2-6}$-alkenyl, Cm-alkynyl, $C_{1-6}$-alkoxy, optionally substituted aryloxy or optionally substituted aryl. In some embodiments the acyl protection group is isobutuyl (—C(O=)CH($CH_3$)$_2$) (also referred to herein as iBu). The term isobuturyl may also be spelt isobutyryl.

Oxazaphospholidine Phosphoramidite

Oxazaphospholidine chiral auxiliary phosphoramidite monomers may be referred to as oxazaphospholidine phosphoramidites, (also referred to as a nucleoside monomer, monomer or amidite herein), such as a nucleoside monomer of formula 1, comprising acetonitrile, the nucleoside monomer, and an aromatic heterocyclic solvent.

In some embodiments, the nucleoside monomer is of formula A:

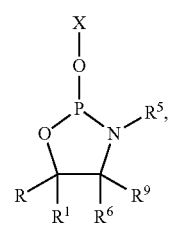

Formula A wherein X is the 3' of a nucleoside, $R^5$ and $R^6$ are independently selected from the group consisting of hydrogen, alkyl, cyclo-alkyl, aryl, heteroaryl, substituted alkyl, substituted cyclo-alkyl, substituted aryl, and substituted heteroaryl, or $R^5$ and $R^6$ together form a heterocyclic ring comprising 3-16 carbon atoms, together with the N atom of formula A;

$R^9$ is hydrogen;

$R^1$ is selected from the groups consisting of hydrogen and $C_1$-3 alkyl; and, R is selected from the groups consisting of aryl, heteroaryl, substituted aryl, substituted heteroaryl, nitro, halogen, cyano, silyl, substituted silyl, sulfone, substituted sulfone (aryl substituted sulfone), fluorene, and substituted fluorine;

wherein, when substituted, R may be substituted with a group selected from the group consisting of: $C_{1-4}$ alkyl group, $C_{6-14}$ aryl group $C_{1-4}$, alkoxy group, $C_{7-14}$ aralkyl group, $C_{1-4}$ alkyl, $C_{6-14}$ aryl group, $C_{1-4}$ alkoxy, $C_{6-14}$ aryl group, or $C_{6-14}$ aryl $C_{1-4}$ alkyl group. Multiple substitutions may be dependently or independently selected from the group consisting of: $C_{1-4}$ alkyl group, $C_6$-14 aryl group $C_{1-4}$, alkoxy group, $C_{7-14}$ aralkyl group, $C_{1-4}$ alkyl, $C_6$-14 aryl group, $C_{1-4}$ alkoxy, $C_{6-14}$ aryl group, or $C_{6-14}$ aryl $C_{1-4}$ alkyl group.

The monomer shown in formula 1 may exist in two chiral isoforms as shown below:

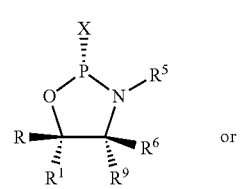

Formula A(i)

or

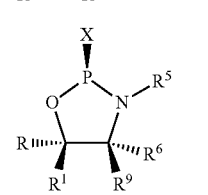

Formula A(ii)

In some embodiments, the oxazaphospholidine chiral auxiliary phosphoramidite monomers is of formula A(i).

In some embodiments, the oxazaphospholidine chiral auxiliary phosphoramidite monomers is of formula A(ii).

In some embodiments, the oxazaphospholidine chiral auxiliary phosphoramidite monomer is of formula 1 or 2:

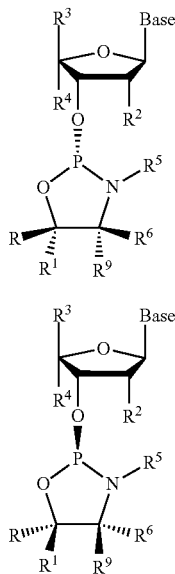

Formula 1

Formula 2 wherein Base is a nucleobase;

R³ is selected from the group consisting of CH₂ODMTr, CH₂-Alkyl-O-DMTr, CH-Me-O-DMTr, CH₂OMMTr, CH₂-Alkyl-O-MMTr, CH(Me)-O-MMTr, CH—R$^a$—O-DMTrR$^b$, and CH—R$^a$—O-MMTrR$^b$; R² is selected from the groups consisting of halo, such as —F, amino, azido, —SH, —CN, —OCN, —CF₃, —OCF₃, —O(R$_m$)-alkyl, —S(R$_m$)-alkyl, —N(R$_m$)-alkyl, —O(R$_m$)-alkenyl, —S(R$_m$)-alkenyl, —N(R$_m$)-alkenyl; —O(R$_m$)-alkynyl, —S(R$_m$)-alkynyl or —N(R$_m$)-alkynyl; O-alkylenyl-O-alkyl, alkynyl, alkaryl, aralkyl, O-alkaryl, O-aralkyl, O(CH₂)₂SCH₃, O—(C$_{1-12}$)₂—O—N(R$_m$)(R$_n$) or O—CH₂C(=O)—N(R$_m$)(R$_n$), —O—(CH₂)₂OCH₃, and —O—CH₃, where each R$_m$ and R$_n$ are independently, H, an amino protecting group or substituted or unsubstituted C$_{1-10}$ alkyl;

R⁴═ is selected from the group consisting of alkyl, cyclo-alkyl, cyclo-heteroalkyl, O-alkyl, S-alkyl, NH-alkyl, and hydrogen;

or R² and R⁴ together designate a bivalent bridge, such as a bivalent bridge consisting of 1, 2, 3 groups/atoms selected from the group consisting of —C(R$^a$R$^b$)—, —C(R$^a$)═C(R$^b$), —C(R$^a$)═N, O, —Si(R$^a$)₂—, S—, —SO₂—, —N(R$^a$)—, and >C═Z;

wherein R$^a$ and, when present R$^b$, each is independently selected from hydrogen, optionally substituted C$_{1-6}$-alkyl, optionally substituted C$_{2-6}$-alkenyl, optionally substituted C$_{2-6}$-alkynyl, hydroxy, optionally substituted C$_{1-6}$-alkoxy, C$_{2-6}$-alkoxyalkyl, C$_{2-6}$-alkenyloxy, carboxy, C$_{1-6}$-alkoxycarbonyl, C$_{1-6}$-alkylcarbonyl, formyl, aryl, aryloxy-carbonyl, aryloxy, arylcarbonyl, heteroaryl, hetero¬aryloxy-carbonyl, heteroaryloxy, heteroarylcarbonyl, amino, mono- and di(C$_{1-6}$-alkylamino, carbamoyl, mono- and di(C$_{1-6}$-alkyl)-aminocarbonyl, amino-C$_{1-6}$-alkyl-aminocarbonyl, mono- and di(C$_{1-6}$-alkylamino-C$_{1-6}$-alkyl-aminocarbonyl, C$_{1-6}$-alkylcarbonylamino, carbamido, C$_{1-6}$-alkanoyloxy, sulphono, C$_{1-6}$-alkylsulphonyloxy, nitro, azido, sulphanyl, C$_{1-6}$-alkylthio, halogen, where aryl and heteroaryl may be optionally substituted and where two geminal substituents R$^a$ and R$^b$ together may designate optionally substituted methylene (═CH₂), wherein for all chiral centers, asymmetric groups may be found in either R or S orientation.

In some embodiments R³ is —CH₂—O-DMTr, R is phenyl, R¹ is hydrogen or methyl and R⁹ is hydrogen.

In some embodiments, the oxazaphospholidine chiral auxiliary phosphoramidite monomer is of formula 9 or 10,

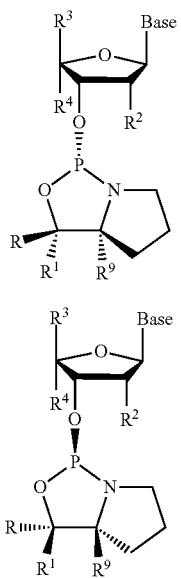

Formula 9

Formula 10

In some embodiments, R⁴ and R² are hydrogen. In some embodiments the nucleoside X is a DNA nucleoside. Representative DNA monomers include the following:

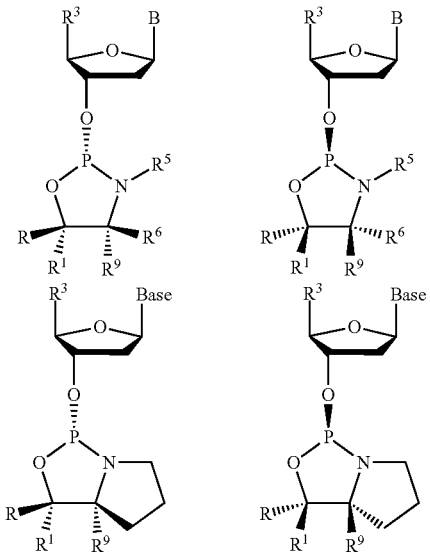

B represents a nucleobase.

In some embodiments wherein the nucleoside X is a DNA nucleoside (i.e R⁴ and R² are hydrogen), R is phenyl, and R¹ is either hydrogen or methyl.

In some embodiments R⁴ and R² form a bivalent bridge. In some embodiments the nucleoside X is a Locked Nucleic Acid nucleoside (LNA). In some embodiments the oxazaphospholidine chiral auxiliary phosphoramidite monomer is of formula 3 or 4 (beta-D-oxy LNA):

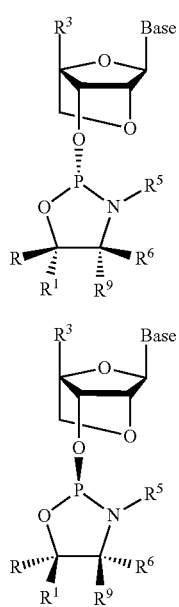

Formula 3

Formula 4

In some embodiments the oxazaphospholidine chiral auxiliary phosphoramidite monomer is an LNA monomer of formula 11 or 12:

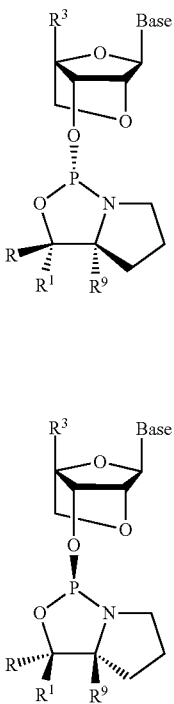

Formula 11

Formula 12

In some embodiments, when the oxazaphospholidine chiral auxiliary phosphoramidite monomer is an LNA monomer, such as those shown in formula 11 or 12, R is phenyl, and $R^1$ is either hydrogen or methyl.

In some embodiments the oxazaphospholidine chiral auxiliary phosphoramidite monomer is of formula 5 or 6:

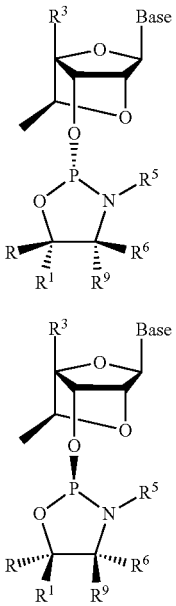

Formula 5

Formula 6

In some embodiments the oxazaphospholidine chiral auxiliary phosphoramidite monomer is of formula 15 or 16:

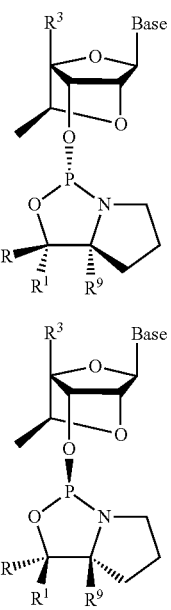

Formula 15

Formula 16

In some embodiments, when the oxazaphospholidine chiral auxiliary phosphoramidite monomer is an LNA monomer of formula 15 or 16, R is phenyl, and $R^1$ is either hydrogen or methyl.

In some embodiments, such as when $R^4$ is hydrogen, $R^2$ may be selected from the group consisting of halo, such as —F, amino, azido, —SH, —CN, —OCN, —CF$_3$, —OCF$_3$, —O($R_m$)-alkyl, —S($R_m$)-alkyl, —N($R_m$)-alkyl, —O($R_m$)-alkenyl, —S($R_m$)-alkenyl, —N($R_m$)-alkenyl; —O($R_m$)-alkynyl, —S($R_m$)-alkynyl or —N($R_m$)-alkynyl; O-alkylenyl-O-alkyl, alkynyl, alkaryl, aralkyl, O-alkaryl, O-aralkyl, $O(CH_2)_2SCH_3$, O—$(CH_2)_2$—O—N($R_m$)($R_n$) or O—$CH_2$C(=O)—N($R_m$)($R_n$), —O—$(CH_2)_2OCH_3$, and —O—$CH_3$, where each $R_m$ and $R_n$ are independently, H, an amino protecting group or substituted or unsubstituted $C_{1-10}$ alkyl. These are referred to as 2' substituted monomers herein.

In some embodiments the oxazaphospholidine chiral auxiliary phosphoramidite monomer is a 2'-O-methoxyethyl (2'MOE) monomer of formula 7 or 8:

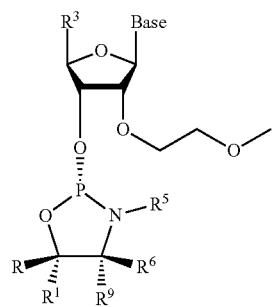

Formula 7

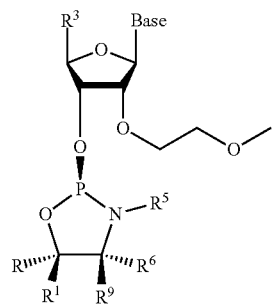

Formula 8

In some embodiments, when the oxazaphospholidine chiral auxiliary phosphoramidite monomer is an 2' substituted monomer, such as a monomer of formula 7, 8, 13 or 14, R is phenyl, and $R^1$ is either hydrogen or methyl.

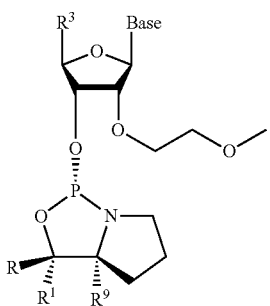

Formula 13

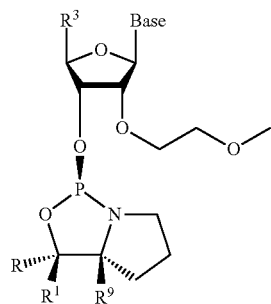

Formula 14

The R and $R^1$ (R/$R^1$) groups of the nucleoside of formula A provide a stereocenter which results in the formation of a Sp or Rp stereodefined phosphorothioate group 3' to the nucleoside when incorporated into an oligonucleotide.

In some embodiments, the stereocenter is in the L configuration, as illustrated in formula A(i), 1, 9, 3, 11, 5, 15, 7 & 13. Such monomer referred to as a L monomer herein which results in the formation of a Sp stereocenter In some embodiments, the stereocenter is in the D configuration, as illustrated in formula A(ii), 2, 10, 4, 12, 6, 16, 8 & 14. Such monomer referred to as a D monomer herein which results in the formation of a Rp stereocenter.

DMF Protected L-LNA-G

As illustrated in the examples, DMF protected L-LNA-G monomers are poorly soluble in acetonitrile solvents.

In some embodiments, the oxazaphospholidine phosphoramidite monomer is not an L-LNA monomer comprising a DMF protected guanine nucleobase (Base).

In some embodiments a DMF protected guanine group has the following structure:

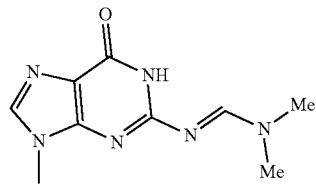 [SMILES: CN(C)/C=N/c1nc2c(ncn2C)c(=O)[nH]1]

In some embodiments, the oxazaphospholidine phosphoramidite monomer is not a monomer of formula 31 or 32

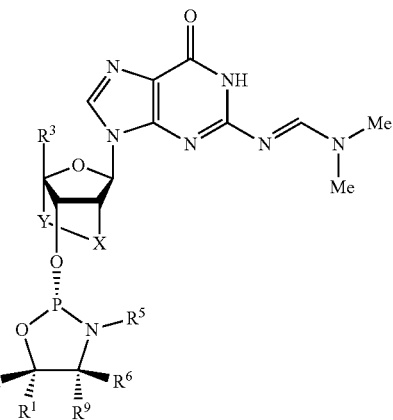

Formula 31

Formula 32

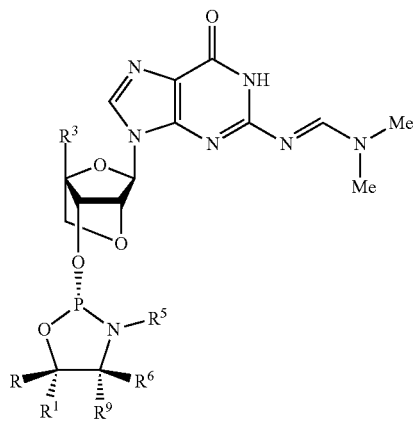

wherein R, $R^1$, $R^3$, $R^5$, $R^6$ & $R^9$ are as according to the monomer of formula 1, and wherein for the monomer of formula 11, X and Y together designate a bivalent bridge (e.g. as per $R^2$ and $R^4$ herein, such as a bridge selected from the group consisting of bridge —C($R^aR^b$)—O—, —C($R^aR^b$) C($R^aR^b$)—O—, —CH$_2$—O—, —CH$_2$ CH$_2$—O—, —CH(CH$_3$)—O—. In some embodiments, X and Y designate the bivalent bridge —CH$_2$—O— (methylene-oxy also known as oxy-LNA) or —CH(CH$_3$)—O— (methyl-methylene-oxy). The —CH(CH$_3$)—O— bridge introduces a chiral center at the carbon atom within the bridge, in some embodiments this is in the S position (for example a nucleoside known in the art as (S)cET—see EP1984381)). In some embodiments, X and Y designate the bivalent bridge —CH$_2$—O— wherein the bridge is in the beta-D configuration (beta-D-oxy LNA). In some embodiments, X and Y designate the bivalent bridge —CH$_2$—O— wherein the bridge is in the alpha-L configuration (alpha-L-D-oxy LNA), In some embodiments, X and Y designate the bivalent bridge —CH$_2$—S— (thio LNA), or —CH$_2$—NH$_2$— (amino LNA). In the embodiments where X and Y together designate a bivalent bridge, $R^3$ may, for example be CH$_2$—O-DMTr or CH$_2$—O-MMTr.

In some embodiments, the oxazapholidine phosphoramidite monomer is not a monomer of formula 33 or 34 formula 33

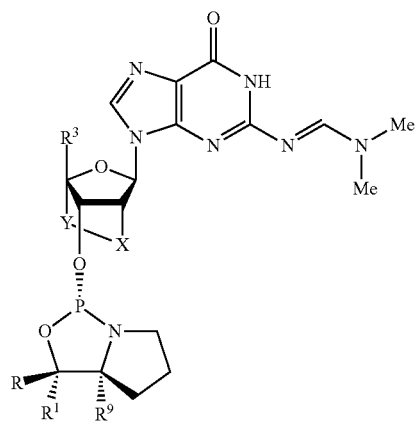

formula 34

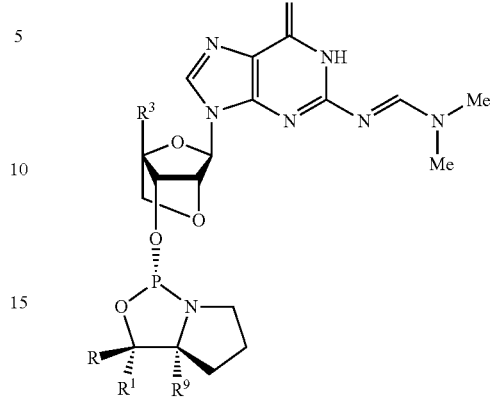

Wherein X, Y, R, $R^1$, $R^9$ and $R^3$ are as per formula 1. The exocyclic oxygen of the guanine base may optionally be protected, e.g. with a cyano group.

In some embodiments, the oxazaphospholidine phosphoramidite monomer is not a monomer of formula 35 or 36 formula 35

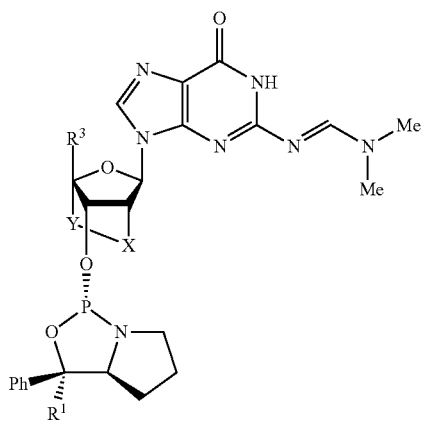

formula 36

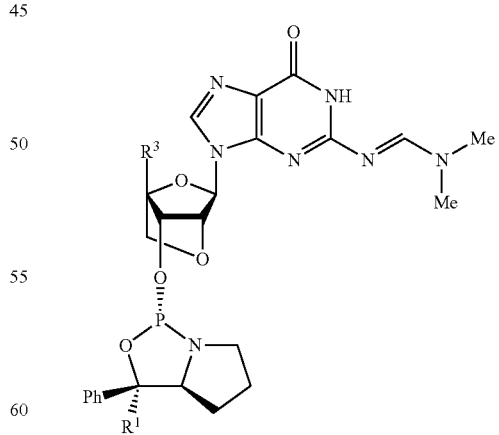

Wherein X, Y, $R^1$ and $R^3$ are as per formula 1. The exocyclic oxygen of the guanine base may optionally be protected, e.g. with a cyano group. In some embodiments of formula 35 or 66, $R^1$ is hydrogen. In some embodiments of formula 35 or 36, $R^3$ is CH$_2$—O-DMTr or CH$_2$—O-MMTr.

In some embodiments, the oxazaphospholidine phosphoramidite monomer of the invention comprises an acyl protected nucleoside (Z).

Acyl Protected L-LNA-G

As illustrated in the examples, DMF protected L-LNA-G monomers are poorly soluble in acetonitrile solvents. However, the inventors have identified that the use of acyl protection groups on the guanine nucleoside of L-LNA-G monomers overcomes the solubility problem.

The exocyclic nitrogen group of guanine is illustrated below (encircled). This group may be protected by an acyl group in LNA monomers the invention, for example an isobutyryl group. Such acyl protected L-LNA-G monomers have been found to be more soluble and stable than the usual DMF protected L-LNA-G monomers, and are therefore particularly useful when the amine containing oxazaphospholidine chiral auxiliary phosphoramidite monomer is a L-LNA-G monomer. The oxygen group may optionally also be protected, e.g. with a cyano group.

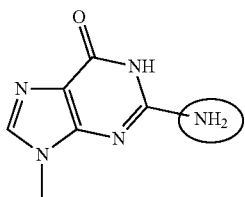

In some embodiments, the oxazaphospholidine phosphoramidite monomer is an L-LNA monomer comprising an acyl protected guanine nucleobase, such as an isobutyryl protected guanine.

In some embodiments, the oxazaphospholidine phosphoramidite monomer is an L-LNA-G monomer of formula 23, 24, 25, 26, 27, 28, 29 or 30:

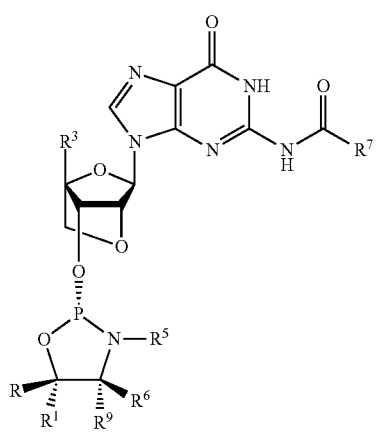

Formula 23

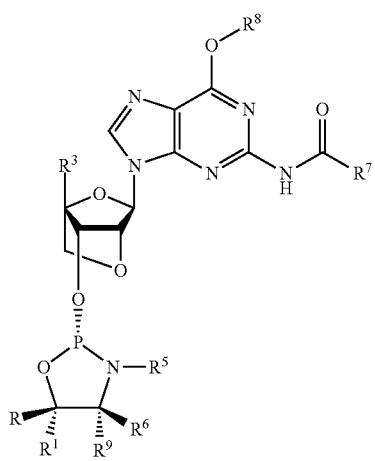

formula 24

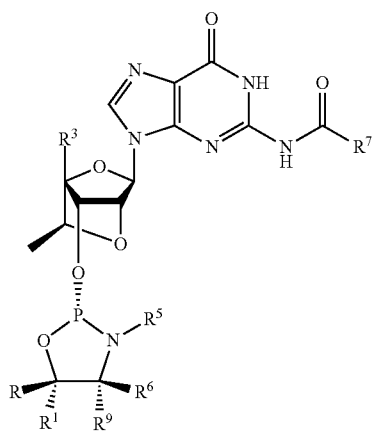

formula 25

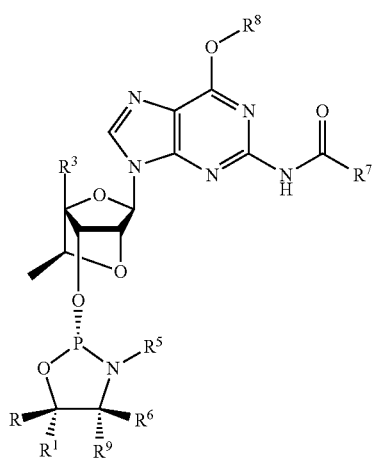

formula 26 formula 27

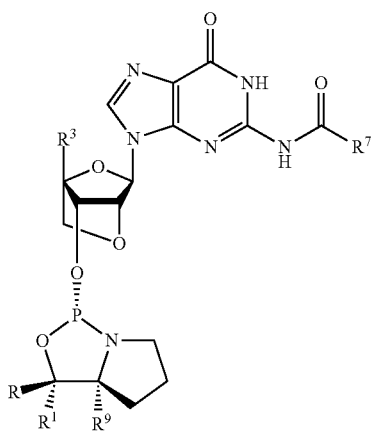

formula 28

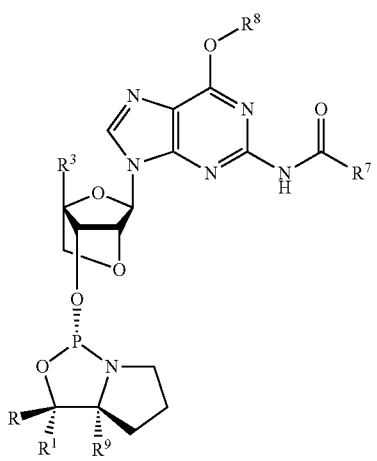

formula 29

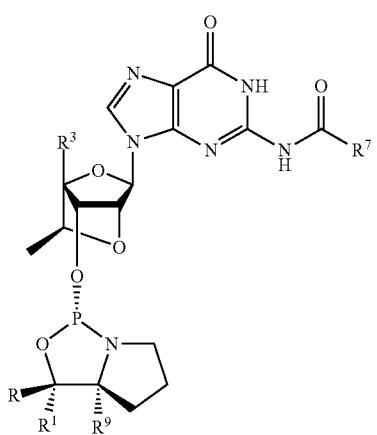

formula 30

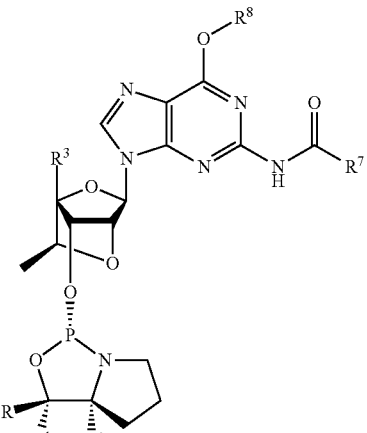

formula 31

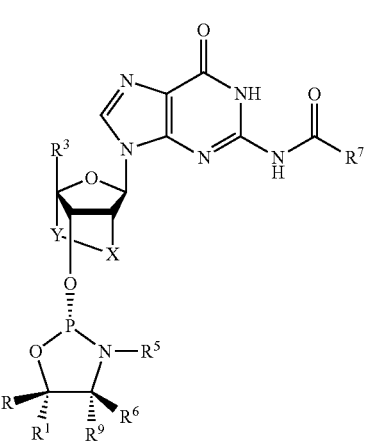

formula 32

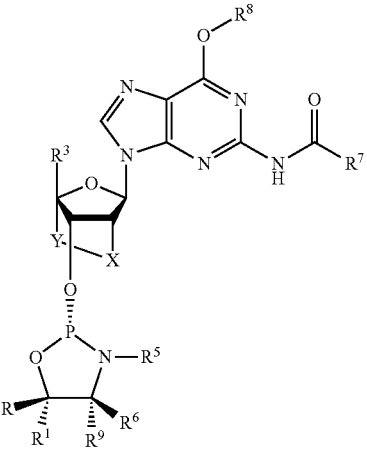

wherein, R, $R^1$, $R^2$, $R^3$, $R^4$, $R^5$, $R^9$ and $R^6$ are as per the compound of the invention, and —C(=O)—$R^7$ is the acyl protecting group on the exocyclic nitrogen of the guanine base, and $R^8$ when present is a protecting group on the guanine exocyclic oxygen. In some embodiments $R^8$ is cyanoethyl. In some embodiments, R is phenyl, $R^1$ is hydrogen or methyl, and $R^3$ is optionally $CH_2$—O-DMTr or $CH_2$—O-MMTr. In some embodiments, $R^7$ is isobutyryl. In formula's 31 and 32, Y and X are as per formula 11.

In some embodiments, such as when the oxazaphospholidine monomer is of formula 3, 11, 5 or 15, the nucleobase (Base) present on the nucleoside of the oxazaphospholidine monomer is a guanine nucleoside wherein the guanine nucleobase group comprises an acyl protection group on the guanine exocyclic nitrogen group.

An "acyl protection group" comprises an acyl group —C(=O)—$R^7$, wherein $R^7$ is a terminal group, for example a group selected from, alkyl-, alkyl-, alkenyl-, alkynyl-, cycloalkyl- and aryl-group; or a group selected from, unsubstituted alkyl-, unsubstituted alkenyl-, unsubstituted alkynyl-, unsubstituted cycloalkyl- or unsubstituted aryl-group; or a group selected from substituted alkyl-, substituted alkenyl-, substituted alkynyl-, substituted cycloalkyl- or substituted aryl-group. In some embodiments $R^7$ may be selected from the group consisting of unsubstituted $C_{1-6}$-alkyl-, unsubstituted $C_{2-6}$-alkenyl-, unsubstituted $C_{3-7}$-cycloalkyl- or unsubstituted phenyl-group or substituted $C_{1-6}$-alkyl-, substituted Cm-alkenyl-, substituted $C_{2-6}$-alkinyl-, substituted $C_{3-7}$-cycloalkyl- or substituted phenyl-group; wherein when substituted, the substituent group may be mono or poly substituted, e.g. with one or more substituents selected from the group consisting of halogen, $C_{1-6}$-alkyl, $C_{2-6}$-alkenyl, Cm-alkynyl, $C_{1-6}$-alkoxy, optionally substituted aryloxy or optionally substituted aryl. In some embodiments the acyl protection group is isobuturyl (—C(O=)CH(CH$_3$)$_2$) (also referred to herein as iBu). The term isobuturyl may also be spelt isobutyryl.

In some embodiments, the oxazaphospholidine monomer is of formula 3, 11, 5 or 15, and the nucleobase (Base) present on the nucleoside of the oxazaphospholidine monomer is a guanine nucleoside wherein the guanine nucleobase group comprises an acyl protection group on the guanine exocyclic nitrogen group. In some embodiments, the acyl protection group present on the guanine exocyclic nitrogen group is isobuturyl. In some embodiments, the "L-LNA-G" oxazaphospholidine monomer is an LNA monomer of formula 1. In some embodiments, the "L-LNA-G" oxazaphospholidine monomer is a high affinity LNA monomer of formula 1.

The R Group on the Chiral Auxiliary

When substituted, R may be substituted with a group selected from the group consisting of: $C_{1-4}$ alkyl group, $C_{6-14}$ aryl group $C_{1-4}$ alkoxy group, $C_{7-14}$ aralkyl group, $C_{1-4}$ alkyl, $C_{6-14}$ aryl group, $C_{1-4}$ alkoxy, $C_{6-14}$ aryl group, or $C_{6-14}$ aryl $C_{1-4}$ alkyl group. Multiple substitutions may be dependently or independently selected from the group consisting of: $C_{1-4}$ alkyl group, $C_{6-14}$ aryl group $C_{1-4}$, alkoxy group, $C_{7-14}$ aralkyl group, $C_{1-4}$ alkyl, $C_{6-14}$ aryl group, $C_{1-4}$ alkoxy, $C_{6-14}$ aryl group, or $C_{6-14}$ aryl $C_{1-4}$ alkyl group.

In some embodiments R is selected from the groups consisting of aryl, heteroaryl, substituted aryl, substituted heteroaryl, nitro, halogen, cyano, silyl, substituted silyl, sulfone, substituted sulfone (aryl substituted sulfone), fluorene, and substituted fluorene.

In some embodiments R is selected from the group consisting of aryl, heteroaryl, substituted aryl and substituted heteroaryl.

In some embodiments R is aryl, such as phenyl.

In some embodiments, when R is substituted aryl, R may be substituted with halide, such as iodide, fluoride, bromide or chloride, such as phenyl substituted with halide, such as iodide, fluoride, bromide or chloride.

In some embodiments $R^1$ is hydrogen. In some embodiments $R^1$ is $C_{1-3}$ alkyl, such as methyl, ethyl or propyl. In some embodiments $R^1$ is methyl.

In some embodiments, R is aryl, such as phenyl and $R^1$ is hydrogen.

In some embodiments, R is aryl, such as phenyl, and $R^1$ is $C_{1-3}$ alkyl, such as methyl, ethyl or propyl.

In some embodiments R is

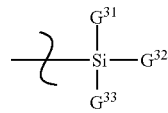

wherein $G^{31}$, $G^{32}$ and $G^{33}$ are independently selected from the groups consisting of $C_{1-4}$ alkyl, $C_{6-14}$ aryl$C_{1-4}$alkoxy, $C_{7-14}$ aralkyl, $C_{1-4}$ alkyl$C_{6-14}$ aryl, $C_{1-4}$ alkoxy$C_{6-14}$ aryl, and $C_{6-14}$ aryl$C_{1-4}$ alkyl.

In some embodiments R is

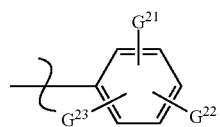

wherein $G^{21}$, $G^{22}$ and $G^{23}$ are independently hydrogen, nitro, halogen, cyano or $C_{1-3}$ alkyl.

In some embodiments R is

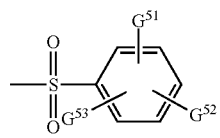

wherein $G^{51}$, $G^{52}$ and $G^{53}$ are independently hydrogen, nitro, halogen, cyano or $C_{1-3}$ alkyl or $C_{1-3}$alkyloxy group.

In some embodiments $R^5$ and $R^6$ together form a heterocylic ring (with the cyclic nitrogen shown in Formula 1)—nucleoside monomers referred to as bicyclic oxazaphospholidine phosphoramidites. The heterocyclic ring may comprise, for example 3-16 carbon atoms, such as 4 carbons atoms.

Bicyclic Oxazaphospholidine Phosphoramidite Monomers

In some embodiments the monomer is a bicyclic oxazaphospholidine phosphoramidite monomer, e.g. in some embodiments $R^5$ and $R^6$ together form a heterocylic ring. In some embodiments $R^5$ and $R^6$ together form a heterocylic ring (with the cyclic nitrogen shown in Formula 1) which comprises 4 carbon atoms, making a total of five atoms in the heterocyclic ring (4 carbon and the nitrogen shown in Formula A or A(i) or A(ii). For example, the compound of the invention may be of formula 9, 10, 11, 12, 13, 14, 15 or 16.

In some embodiments $R^5$ and $R^6$ together form a heterocylic ring (with the cyclic nitrogen shown in Formula I) which comprises 4 carbon atoms, making a total of five atoms in the heterocyclic ring (4 carbon and the nitrogen shown in Formula 1), and R is aryl, such as phenyl, $R^1$ is hydrogen or methyl. $R^9$ is hydrogen.

Nucleobase

In some embodiments B is a nucleobase selected from the group consisting of adenine, guanine, cytosine, thymidine, uracil, xanthine, hypoxanthine, 5-methylcytosine, isocytosine, pseudoisocytosine, 5-bromouracil, 5-propynyluracil, 6-aminopurine, 2-aminopurine, inosine, diaminopurine, and 2-chloro-6-aminopurine.

In some embodiments B is a purine nucleobase. In some embodiments Base (B) is a pyrimidine nucleobase. In some embodiments, Base (B) is adenine. In some embodiments, Base (B) is thymidine. In some embodiments, Base (B) is guanine. In some embodiments, Base (B) is cytosine. In some embodiments, when Base (B) is cytosine, it is 5-methyl-cytosine.

It should be understood that for use in oligonucleotide synthesis the nucleobase group (Base) may be protected in the amidite monomers (thymidine is often used without a protection group). Suitable protection groups include dimethyformamide (DMF), dimethoxytrityl (DMT) or an acyl protection group, such as isobutyryl (iBu), or an acetyl protection group (Ac) or a benzoyl protection group (Bz).

In some embodiments, e.g. when the monomer is an L-LNA-G (guanine) the nucleobase (Base (B)) is other than DMF protected guanine (G). $R^3$= is selected from the group consisting of $CH_2ODMTr$, $CH_2$-Alkyl-O-DMTr, CH-Me-O-DMTr, $CH_2OMMTr$, $CH_2$-Alkyl-O-MMTr, CH(Me)-O-MMTr, CH—$R^a$—O-DMTr$R^b$, and CH—$R^a$—O-MMTr$R^b$.

High Affinity Monomers

In some embodiments, when incorporated into an oligonucleotide, the nucleoside (Z) confers a higher binding affinity to a complementary RNA target than an equivalent DNA nucleoside. Such nucleosides are referred to as high affinity nucleosides. Examples of high affinity nucleosides include 2'-O-MOE, 2'-fluoro, 2'-O-methyl, and LNA nucleosides. In the embodiments, where the nucleoside is a high affinity nucleoside $R^3$ may, for example, be $CH_2$—O-DMTr or $CH_2$—O-MMTr.

In some embodiments, $R^2$ is selected from the group consisting of fluoro (—F), —O—$(CH_2)_2OCH_3$, and —O—$C_{1-3}$ alkyl, such as —O—$CH_3$. In such embodiments, optionally $R^4$ is hydrogen.

In some embodiments, the nucleoside is a LNA nucleoside (also known as a bicyclic nucleoside) comprising a 2'-4' bridge (biradicle).

In some embodiments, $R^2$ and $R^4$ together designate a bivalent bridge selected from the group consisting of bridge —C($R^aR^b$)—O—, —C($R^aR^b$) C($R^aR^b$)—O—, —$CH_2$—O—, —$CH_2$ $CH_2$—O—, —CH($CH_3$)—O—. In some embodiments, $R^2$ and $R^4$ designate the bivalent bridge —$CH_2$—O— (methylene-wry also known as oxy-LNA) or —CH($CH_3$)—O— (methyl-methylene-oxy).

The —CH($CH_3$)—O— bridge introduces a chiral center at the carbon atom within the bridge, in some embodiments this is in the S position (for example a nucleoside known in the art as (S)cET—see EP1984381)). In some embodiments, $R^2$ and $R^4$ designate the bivalent bridge —$CH_2$—O— wherein the bridge is in the beta-D position (beta-D-oxy LNA). In some embodiments, $R^2$ and $R^4$ designate the bivalent bridge —$CH_2$—O— wherein the bridge is in the alpha-L position (alpha-L-D-oxy LNA), In some embodiments, $R^2$ and $R^4$ designate the bivalent bridge —$CH_2$—S— (thio LNA), or —$CH_2$—$NH_2$— (amino LNA). In the embodiments where $R^2$ and $R^4$ together designate a bivalent bridge, $R^3$ may, for example be $CH_2$—O-DMTr or $CH_2$—O-MMTr.

In some embodiments where the nucleoside (X) is a bicyclic nucleotide (LNA) such as beta-D-oxy LNA or 6'methyl beta-D-oxy-LNA (also referred to as e.g. (S)cET), R is aryl, such as phenyl, and $R^1$ is hydrogen or $C_{1-3}$ alkyl. In such am embodiment, $R^5$ and $R^6$ may together form a heterocylic ring, such as a five membered heterocyclic ring, as described herein.

5'-OH Group of a Nucleoside and Solid Support

The method for the synthesis of a stereodefined phosphorothioate oligonucleotide according to the present invention comprises the step of coupling to a 5'-OH group of a preceding nucleoside. The preceding nucleoside may be attached to a solid support (oligonucleotide synthesis support), either directly or via further other nucleotides, and prior to the coupling step (i), the 5'-OH group may be deprotected (e.g. via removal of the 3' protection group (which may be as defined as $R^3$ herein, such as DMTr (—$CH_2$—O-DMTr). Suitable oligonucleotide supports include a polystyrene or controlled pore glass support containing a UnyLinker moiety (see Ravikumar et al., Org. Process Res. Dev., 2008, 12 (3), pp 399-410) or a nucleoside 3'-succinate linkage:

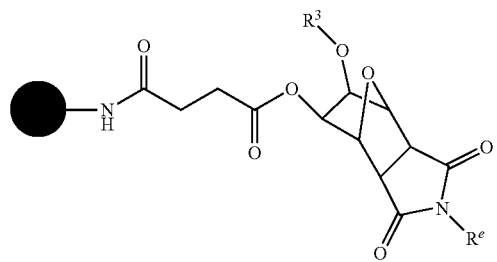

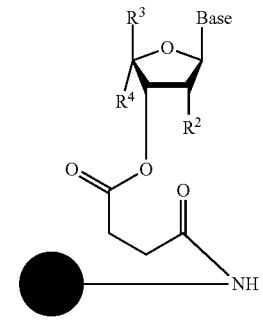

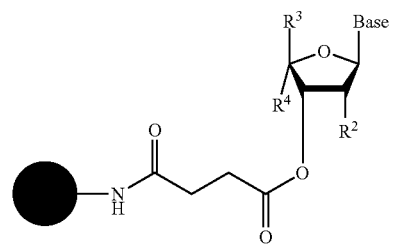

wherein $R^e$ is $R^e$ is aryl or C1-10 alkyl, such as phenyl, isopropyl or methyl, and the solid circle represents the solid support matrix, such as polystyrene or controlled pore glass. UnyLinker supports where $R^e$ is either phenyl or methyl are commercially available and are widely used in oligonucleotide synthesis.

In some embodiments $R^e$ may be other than phenyl or methyl, for example other alkyl or aryl groups may be used.

Specific support matrixes include:

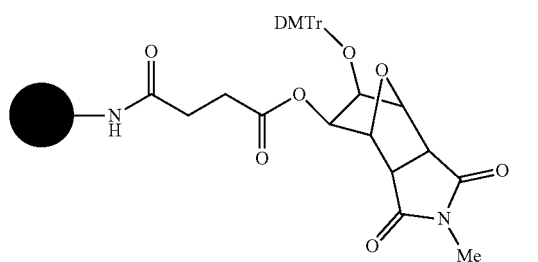

or

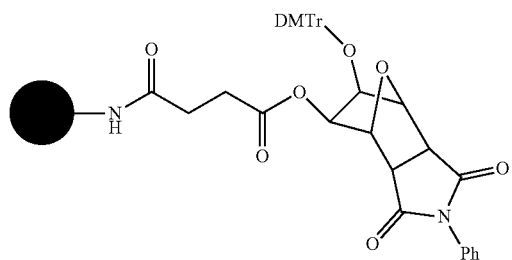

The preceding nucleoside, when it is the first nucleoside coupled to the solid support may be represented as follows:

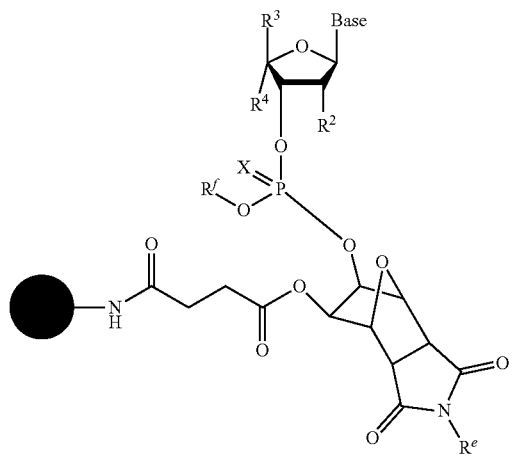

or, if there are further preceding nucleosides already attached to the solid support, the preceding nucleotide attached to the solid support may be represented as follows:

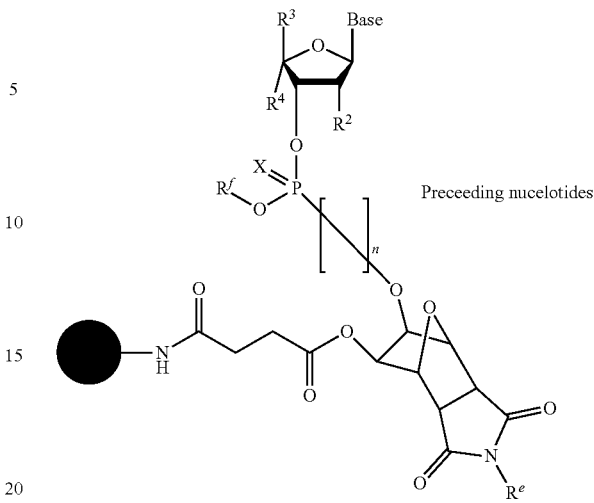

wherein $R^2$, $R^4$, $R^3$ are as defined per the oxazaphospholidine chiral auxiliary phosphoramidite monomer, $R^e$ is Re is aryl or C1-10 alkyl, such as phenyl, isopropyl or methyl, $R^f$ is H or cyanoethyl, X is either O or S, and n represents the number of preceding nucleotides. n may for example be 1, 2, 3, 4, 5, 6, 7, 8, 9, 10, 11, 12, 13, 14, 15, 16, 17, 18, 19, 20, 21, 22, 23, 24 or 25.

Deblocking may be performed prior to the coupling step, by removal of the $R^3$ group (such as DMTr) to leave a 3'-OH group. Deblocking may be performed using a solution of an acid, such as 3% trichloroacetic acid (TCA) or 3% dichloroacetic acid (DCA), in an inert solvent (e.g. dichloromethane or toluene). When $R^3$ group contains a DMTr group, the orange-colored DMT cation formed is washed out; the step results in the solid support-bound oligonucleotide precursor bearing a free 5'-terminal hydroxyl group:

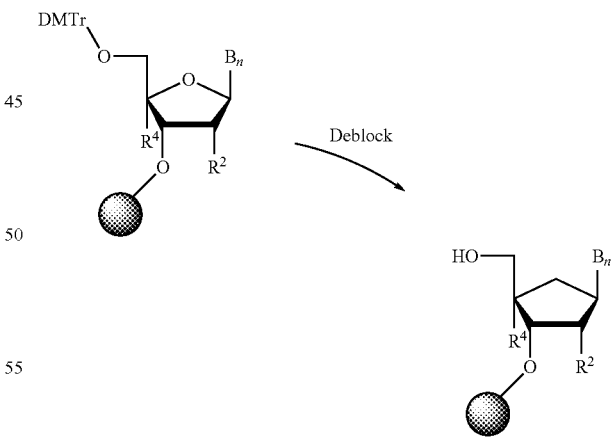

(for illustrative purposes only)

Coupling Step

The coupling step (i) comprises the reaction of the oxazaphospholidine chiral auxiliary phosphoramidite monomer (the amidite) to the 5'-OH group of the preceding monomer. The coupling step may be performed in a suitable solvent, such as acetonitrile and in the presence of an activator.

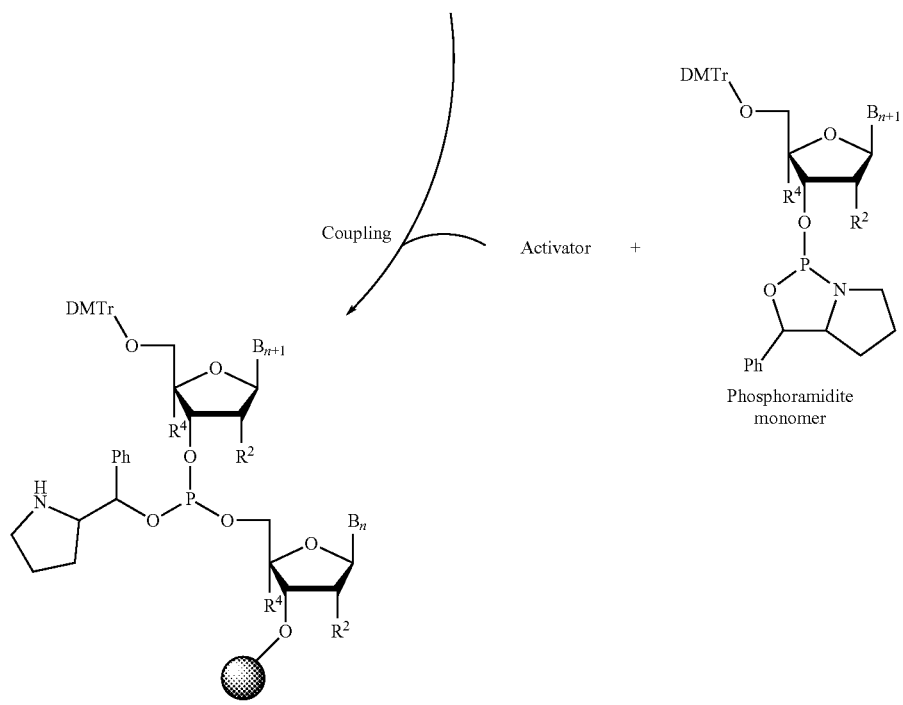

(For Illustrative Purposes Only)

In a preferred embodiment, the coupling step is performed in an acetonitrile solvent composition comprising acetonitrile and an aromatic heterocyclic solvent, and optionally an activator. In some embodiments the aromatic heterocyclic solvent is pyridine.

Coupling Solvents

The coupling solvent used in the method of the invention may be an acetonitrile and aromatic heterocyclic base solvent.

The invention provides for a process for coupling an oxazaphospholidine phosphoramidite monomer to a 5'-terminus of a nucleoside or oligonucleotide, or a hydroxyl group attached to a solid support (e.g. unylinker), comprising the step of reacting the nucleoside, the oligonucleotide or solid support, with the oxazaphospholidine phosphoramidite monomer, wherein said reaction takes place in an acetonitrile solvent composition comprising acetonitrile and an aromatic heterocyclic solvent.

The invention provides for a process for coupling an oxazaphospholidine phosphoramidite monomer to a 5'-terminus of a nucleoside or oligonucleotide, or a hydroxyl group attached to a solid support (e.g. unylinker), comprising the step of reacting the nucleoside, the oligonucleotide or solid support, with the oxazaphospholidine phosphoramidite monomer, wherein said reaction takes place in an acetonitrile solvent composition comprising acetonitrile and an aromatic heterocyclic solvent, and an activator.

The invention provides for a method for oligonucleotide synthesis comprising the process for coupling an oxazaphospholidine phosphoramidite monomer to a 5'-terminus of a nucleoside or oligonucleotide of the invention.

The invention provides for an acetonitrile solution composition comprising an oxazaphospholidine phosphoramidite monomer, acetonitrile and an aromatic heterocyclic solvent.

The invention provides for a method for dissolving oxazaphospholidine phosphoramidite monomer said method comprising adding the monomer to a solvent composition comprising acetonitrile and an aromatic heterocyclic solvent, and optionally an activator.

The invention provides for the use of an aromatic heterocyclic solvent to enhance the stability and/or solubility of a oxazaphospholidine phosphoramidite in acetonitrile.

The invention provides for the use of an aromatic heterocyclic solvent to enhance the reactivity, e.g. the reactivity in an oligonucleotide synthesis coupling step, of an oxazaphospholidine phosphoramidite in acetonitrile.

In some embodiments, the aromatic heterocyclic solvent has a pKa of 4-7 or from 7-17 in water at 20° C.

In some embodiments, the aromatic heterocyclic solvent is an aromatic heterocyclic base.

In some embodiments, the aromatic heterocyclic solvent is an aromatic heterocyclic acid.

In some embodiments, the aromatic heterocyclic solvent is selected from the group consisting of pyridine, 2-picoline, 4-picoline, 3-picoline, lutidine, and pyrrole.

In some embodiments, the aromatic heterocyclic solvent is pyridine, such as between 0.5 and 5% pyridine in acetonitrile.

In some embodiments, the concentration (v/v), of aromatic heterocyclic solvent in acetonitrile is between about 0.1% and about 50% (v/v).

In some embodiments, the concentration (v/v), of aromatic heterocyclic solvent in acetonitrile is between about 0.5% and about 10%, such as between about 1% and about 5%, such as between about 2-3%, such as about 2.5%.

In some embodiments, the activator comprises N-methylimidazole.

In some embodiments, the solvent composition comprises N-methylimidazole in a concentration of 0.01-about 1M N-methylimidazole, such as about 0.1M N-methylimidazole.

In some embodiments, the activator comprises 4,5-dicyanoimidazole (DCI), tetrazole, or 5-(Benzylthio)-1H-tetrazole.

In some embodiments, the solvent composition comprises about 0.5-about 2M DCI.

Sulphurization Prior to Amine Protection

After the coupling step, in some embodiments the coupled monomer undergoes a sulphurization reaction. Sulphurization may be performed by treatment with a sulphurizing reagent, such as 3H-1,2-Benzodithiol-3-one-1,1-dioxide or phenyl acetyl disulfide, or xanthane hydride in a suitable solvent such as acetonitrile and optionally and aromatic heterocyclic solvent such as pyridine, or 3-methylpyridine.

In some embodiments, sulfurization is performed in 0.1M solution of xanthane hydride in acetonitrile and pyridine 1:1 v/v. Sulfurization is typically performed at room temperature.

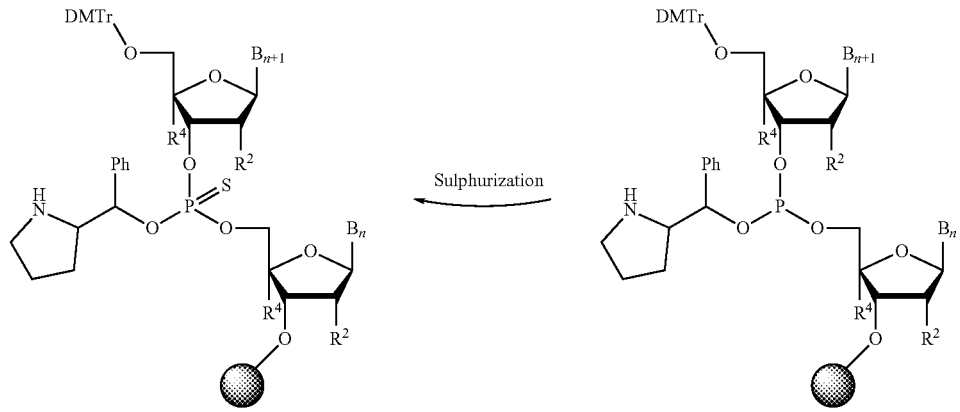

(for illustrative purposes only)

Alternatively, sulphurization may be performed after the amine protection step (ii).

Amine Protection

Step (ii) of the method of the invention comprises the protection of the amine group of the oxazaphospholidine chiral auxiliary with a carbamate protection group:

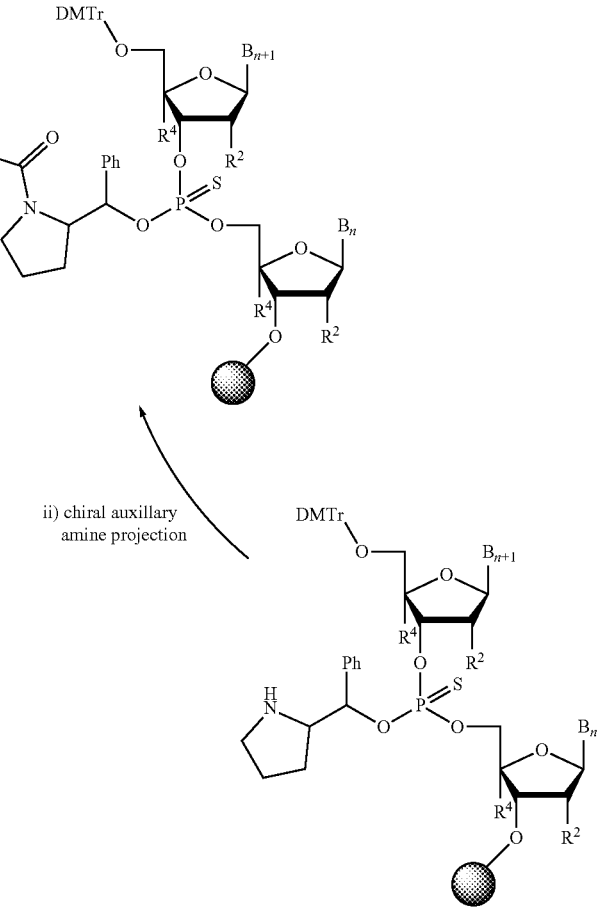

(for illustrative purposes only)

Therefore, step (ii) comprises reacting a carbamate precursor and the coupled an amine containing chiral auxiliary phosphoramidite monomer provided in step (i), under conditions to allow the protection of the nitrogen of the chiral auxiliary with the carbamate protection group, such as in a suitable solvent optionally containing a base, such as a non-nucleophilic base, such as N,N-Diisopropylethylamine Alternatively stated, during step ii), a carbamate precursor is coupled to the amine group of the oxazaphospholidine chiral auxiliary. In some embodiments the carbamate precursor is selected from the group consisting of:

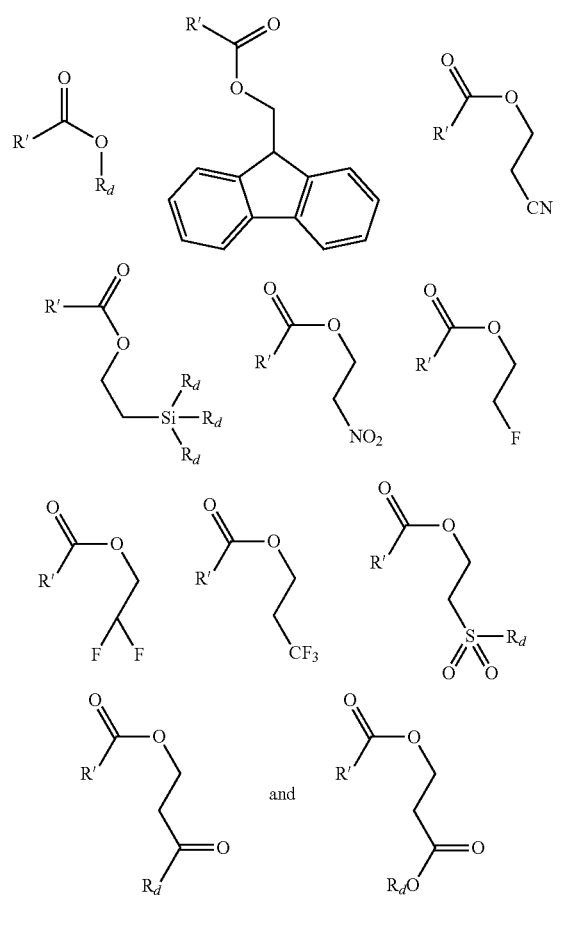

where in $R_d$ is selected from the group consisting of hydrogen, optionally substituted $C_{1-10}$ alkyl-, optionally substituted $C_{2-6}$ alkenyl-, optionally substituted $C_{2-6}$ alkynyl-, optionally substituted $C_{3-7}$ cycloalkyl-, optionally substituted $C_{1-10}$ alkyloxy or an aryl-group, and R' is a leaving group, such as a leaving group selected from the group consisting of

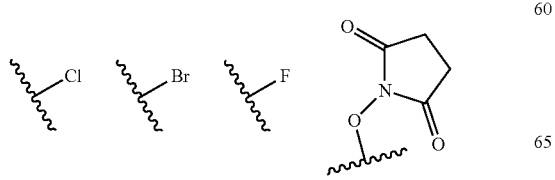

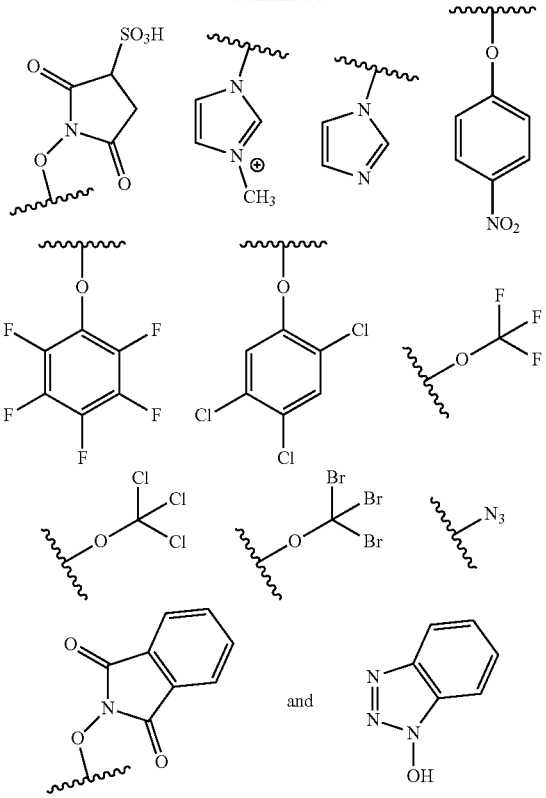

In some embodiments, the carbamate precursor is

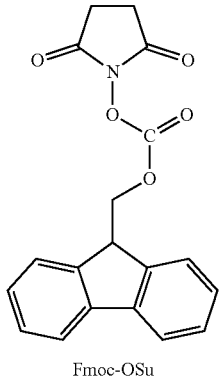 [SMILES: O=C(OCC1c2ccccc2-c2ccccc21)ON1C(=O)CCC1=O]

Fmoc-OSu

In some embodiments, the carbamate precursor is

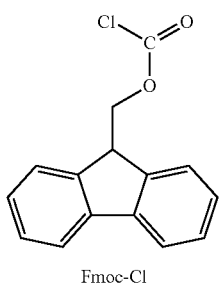 [SMILES: "Fmoc-Cl" ; O=C(Cl)OCC1c2ccccc2-c2ccccc21]

Fmoc-Cl

In some embodiments, the carbamate precursor is

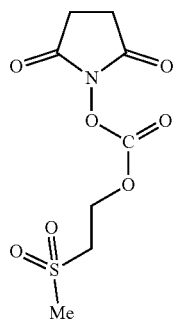 [SMILES: CS(=O)(=O)CCOC(=O)ON1C(=O)CCC1=O]

In some embodiments, the carbamate precursor is

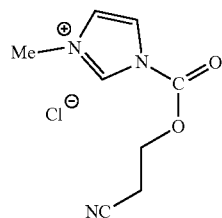

In some embodiments, the carbamate precursor is

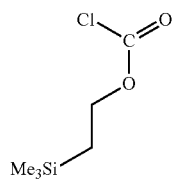

The Carbamate Protected Amine

In some embodiments, the amine carbamate protection group is a substituted ethyl carbamate protection group of formula:

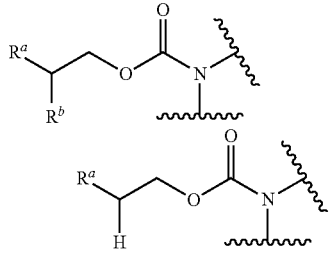

wherein N is the nitrogen present in the chiral auxiliary, and $R^a$, and optionally when present, $R^b$, is a group independently selected from the group consisting of —CN, —SO$_2$R$^c$, —SiR$^c{}_3$, —F, —Cl, —CF$_3$, and —CO—R$^c$, wherein R$^c$ is independently selected from the group consisting of hydrogen, optionally substituted C$_{1-10}$ alkyl-, optionally substituted C$_{2-6}$ alkenyl-, optionally substituted C$_{2-6}$alkynyl-, optionally substituted C$_{3-7}$ cycloalkyl-, optionally substituted C$_{1-10}$ alkyloxy or an aryl-group; or R$^b$ is selected from the group consisting of hydrogen, optionally substituted C$_{1-10}$ alkyl-, C$_{2-6}$ alkenyl-, C$_{2-6}$ alkynyl-, C$_{3-7}$cycloalkyl- and an aryl-group;

or R$^a$ and R$^b$ together form a fluorenyl group (as illustrated by the Fmoc embodiment).

In some embodiments, R$^a$, and optionally when present, R$^b$ are electron withdrawing groups. Electron withdrawing groups allow for a beta-elimination to take place so that the chiral auxiliary can be deprotected under alkaline conditions.

In some embodiments R$^b$ is hydrogen.

In some embodiments, the amine carbamate protection group is an optionally substituted 2'-sulfonyl carbamate protection group of formula:

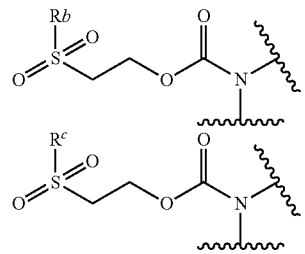

wherein N is the nitrogen present in the chiral auxiliary, and wherein R$^c$ is independently selected from the group consisting of hydrogen, optionally substituted C$_{1-10}$ alkyl-, optionally substituted C$_{2-6}$ alkenyl-, optionally substituted C$_{2-6}$alkynyl-, optionally substituted C$_{3-7}$cycloalkyl-, optionally substituted C$_{1-10}$ alkyloxy or an aryl-group;

In some embodiments R$^b$ is optionally substituted C$_{1-10}$ alkyl or an aryl group, such as phenyl.

In some embodiments the amine carbamate protection group [referred to in step (ii)] is selected from the group consisting of

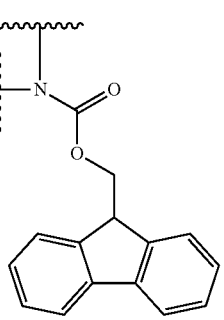
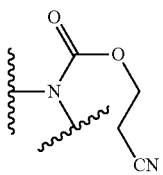
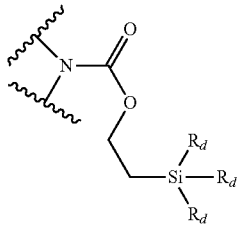
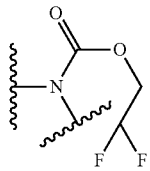
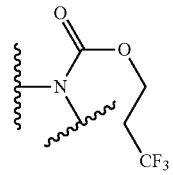

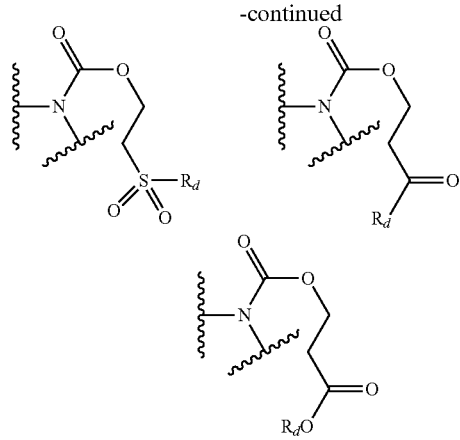

wherein the N is the N present in the chiral auxiliary, and $R_d$ is selected from the group consisting of hydrogen, optionally substituted $C_{1-10}$ alkyl-, optionally substituted $C_{2-6}$ alkenyl-, optionally substituted $C_{2-6}$ alkynyl-, optionally substituted $C_{3-7}$ cycloalkyl-, optionally substituted $C_{1-10}$ alkyloxy or an aryl-group. In some embodiments, $R_d$ is a methyl substituted phenyl group.

In some preferred embodiments, the carbamate protection group is Fmoc:

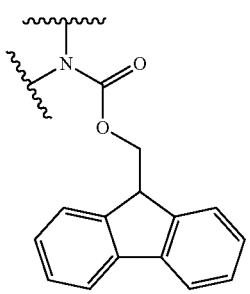 [SMILES: *N(*)C(=O)OCC1c2ccccc2-c2ccccc21]

In some preferred embodiments, the carbamate protection group is a cyano-ethyl carbamate:

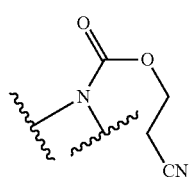 [SMILES: *N(*)C(=O)OCCC#N]

The following reaction schemes illustrate the reaction between selected carbamate precursors and the amine group on the chiral auxiliary:

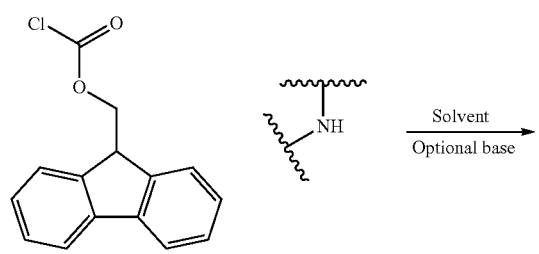

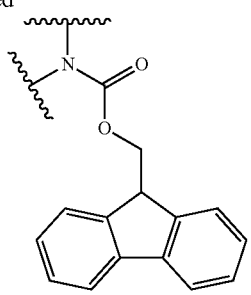

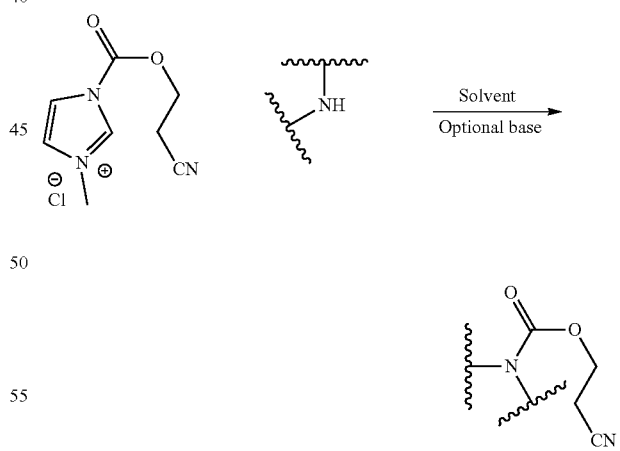

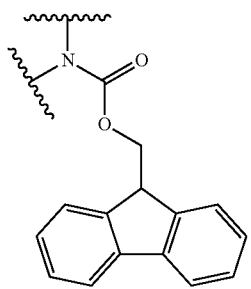

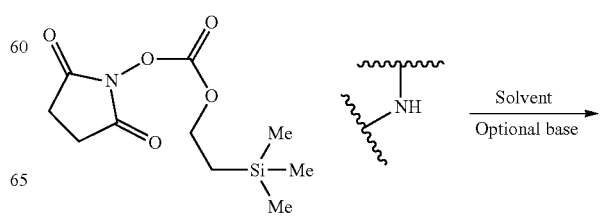

35
-continued

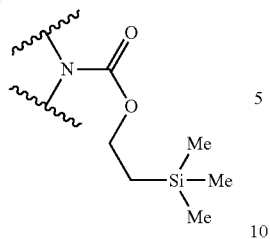

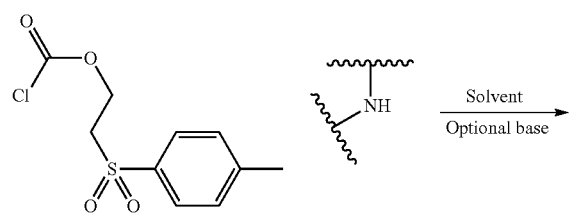

36
-continued

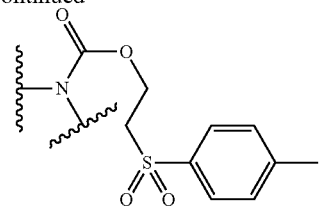

Sulphurization after Amine Protection

After the protection of the amine group of the chiral auxiliary, if not performed prior to amine protection, the coupled and amine protected monomer undergoes a sulphurization reaction.

Sulphurization may be performed by treatment with a sulphurizing reagent, such as 3H-1,2-Benzodithiol-3-one-1,1-dioxide or phenyl acetyl disulfide, or Xanthane Hydride in a suitable solvent such as acetonitrile and optionally and aromatic heterocyclic solvent such as pyridine, or 3-methylpyridine.

In some embodiments, sulfurization is performed in 0.1M solution of xanthane hydride in acetonitrile and pyridine 1:1 v/v. Sulfurization is typically performed at room temperature.

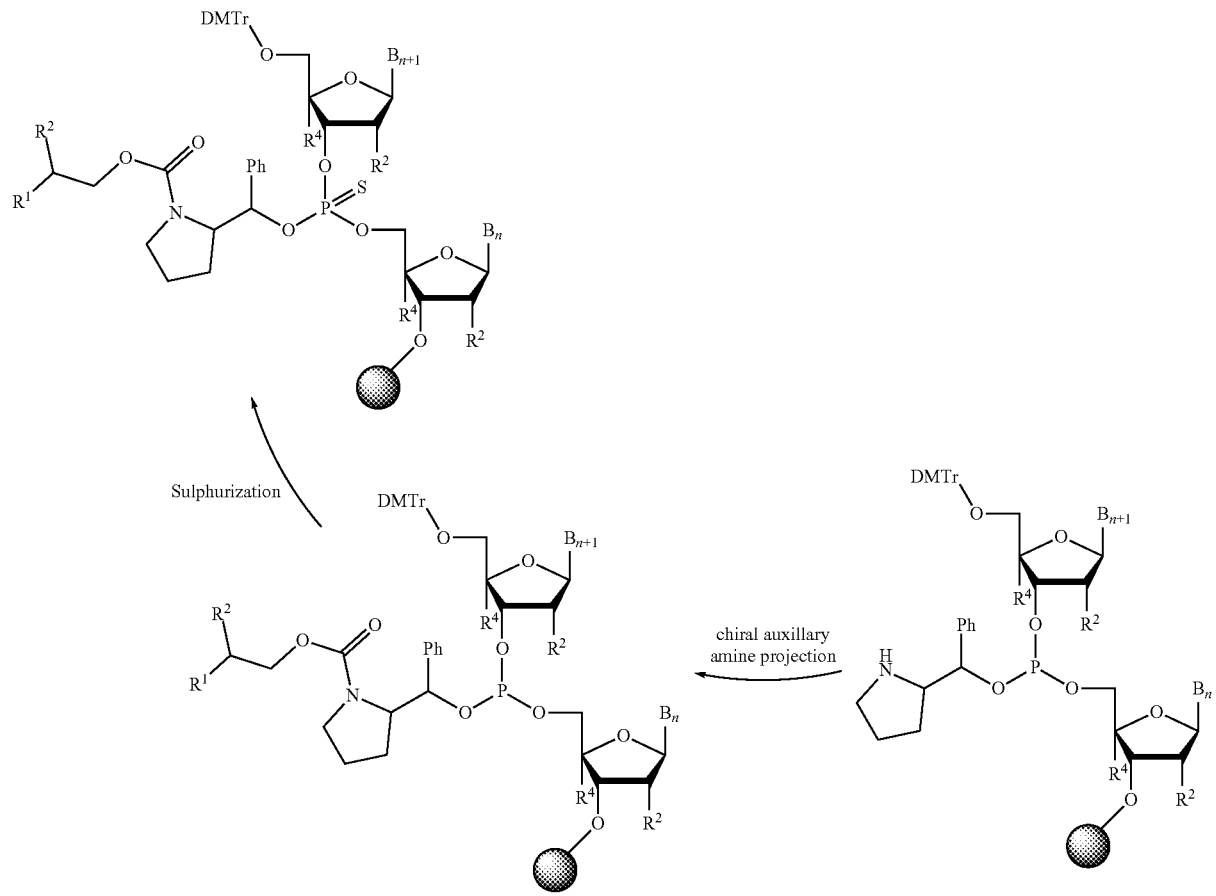

(for illustrative purposes only)

Optional Capping Step

In some embodiments, a capping step is performed subsequent to the chiral auxiliary amine protection step (ii) and the sulphurization step (iii), irrespective of the order of the steps (ii) then (iii) or (iii) and then (ii). Capping is the process where unreacted preceding nucleoside —OH groups are blocked from further chain elongation preventing the formation of oligonucleotides with internal base deletions (n−1) shortmers. Capping may be performed using a solution of acetic anhydride and N-methyl imidazole in one or more solvents (typically acetonitrile, pyridine and/or THF) In some embodiments, no capping step is performed during the elongation cycle comprising steps (i), (ii) and (iii). Capping steps may or may not be used in other elongation cycles during the method of synthesis of the oligonucleotide. In some embodiments, capping is performed subsequent to sulfurization, as capping prior to sulfurization can lead to an increase in the levels of phosphodiester linkages within the oligonucleotide.

Further Elongation Cycles

Once sulphurization and chiral auxiliary amine protection, and optionally capping has been completed, the product may either continue to a further (chain elongation) cycle of oligonucleotide synthesis or may proceed to the post elongation deprotection, chiral auxiliary removal and cleavage from the solid support.

In some embodiments, the method of oligonucleotide synthesis comprises a further 1, 2, 3, 4, 5, 6, 7, 8, 9, 10, 11, 12, 13, 14, 15, 16, 17, 18, 19, 20, 21, 22, 23, 24 or 25 elongation cycles. Such elongation cycles may be as according to steps (i)-(iii) of the method of the invention (or steps b)-f) in the following method of the invention:

Oligonucleotide Synthesis Methods

The invention provides for a method of oligonucleotide synthesis comprising the following steps:
a) provision of a solid support comprising a nucleoside (the preceding nucleoside) with a blocked terminal —OH group (a terminal 5'-OH group);
b) unblocking of the terminal —OH group of the preceding nucleoside;
c) coupling an oxazaphospholidine chiral auxiliary phosphoramidite monomer to the unblocked 5'-OH group of the preceding nucleoside;
d) protecting the amine group of the oxazaphospholidine chiral auxiliary with a carbamate protection group;
e) sulphurization of the phosphorus atom of the oxazaphospholidine chiral auxiliary, either prior to or subsequent to the protection step (d);
f) optionally capping any unreacted terminal 5'-OH groups, wherein the capping step is performed after the sulfurization step (e) or in the embodiment where sulfurization is performed prior to step (d), the capping step may be performed after step (d);
g) optionally repeating steps b)-f) (further chain elongation cycles);
h) Removal of the carbamate protection group,
i) Removal of the chiral auxiliary group(s)
j) Cleavage of the oligonucleotide from the solid support. wherein steps h), i) and j) are performed either sequentially or simultaneously, or step h) is performed prior to the step of removal of the chiral auxiliary and cleavage from the solid support.

In some embodiments, steps b) to f) are repeated 7-25 times, such as 8, 9, 10, 11, 12, 13, 14, 15, 16, 17, 18, 19, 20, 21, 22, 23 and 24 times, in the oligonucleotide synthesis, such as 7-16 times. In some embodiments the reiteration of steps b)-f) are consecutive cycles in the oligonucleotide synthesis.

In some embodiments, after step g) or after step h), an optional amine wash step is performed. The amine wash step refers to an optional procedure used in oligonucleotide synthesis wherein prior to exposure of the oligonucleotide to the strong basic conditions used in the cleavage step the oligonucleotide is treated with a solution of a weak base in an organic solvent, such as treatment with 20% diethylamine in acetontrile, or 1:1 triethylamine/acetonitrile. The amine wash results in the removal of cyanoethyl phosphate protection groups without cleavage of the oligonucleotide from the solid support. The benefit of including an amine wash results in the avoidance of unwanted cyanothyl adducts, such as acrylonitrile, which form due to a side reaction of the cyanoethyl phosphate protection group, and heterocyclic bases, particularly thymine. In some embodiments, the removal of the orthogonal protection group on the chiral auxiliary (step h), may be performed during the amine wash step (i.e. step h may be a combined amine wash and carbamate deprotection step) may combine both the removal of the cyanoethyl phosphate protection group, and the orthogonal protection group, e.g. a cyanoethyl carbamate protection group present on the amine of the chiral auxiliary. In some embodiments, the amine wash may remove both the cyanoethyl protection group, carbamate protection group and the chiral auxiliary.

Alternatively, the carbamate protection group may be removed prior to an amine wash step, such as when the carbamate protection group is other than a cyanoethyl protection group, for example when the carbamate protection group is an Fmoc protection group or a 2'-sulfonyl carbamate. Alternatively, the carbamate protection group may be removed subsequent to an amine wash step, such as when the carbamate protection group is other than a cyanoethyl protection group, for example when the carbamate protection group is an Fmoc protection group or a 2'-sulfonyl carbamate.

In some embodiments, after step j) the oligonucleotide may be purified. The purification step i) may use any suitable method for oligonucleotide purification such as ion exchange purification or reversed phase chromatography, or both ion exchange purification and reversed phase chromatography. In some embodiments purification comprises the sequential steps: a) ion exchange purification, b) desalting, e.g. via diafiltration, followed by c) lyophilisation and d) reversed phase chromatography. Prior to purification it is typical that the ammonium hydroxide is either removed or at least diluted. Alternatively, DMT-ON reversed phase purification followed by detritylation is also an option for purifying oligonucleotides (see Capaldi and Scozzari, Chapter 14, Antisense Drug Technology: Principles, Strategies, and Applications, CRC Press 2008.

As the oxazaphospholidine phosphoramidite monomer introduces either a Sp or Rp phosphorothioate internucleoside linkage the method of the invention may be used to synthesize a stereodefined oligonucleotide. The invention therefore provides for improved methods of synthesising stereodefined phosphorothioate oligonucleotides. In some embodiments, in addition to incorporation of stereodefined phosphorothioate internucleoside linkages, the method of synthesis may, through use of standard phosphoramidite monomers, incorporate stereorandom internucleoside linkages. The method of the invention may therefore comprise elongation cycles according to the present invention which result in stereodefined internucleoside linkages 3' to the introduced monomer, as well as other elongation cycles which use standard phosphoamidite monomers, which introduce stereorandom internucleoside linkages.

FIGS. 1, 2 & 3 provide illustrative examples of oligonucleotide synthesis methods of the present invention.

Carbamate Protection Group Removal

Once chain elongation has been completed, the carbamate protection groups on the amine of the chiral auxiliary are removed. The removal of the carbamate protection group can be achieved much faster and at lower temperatures that the methods used in the prior art (Oka et al). Typically, about four hours or less is sufficient. As is illustrated in the examples, orthogonal carbamate deprotection can be routinely achieved in less than about 3 hours, such as less and or about 2 hours such as less than or about 1 hour. In some embodiments orthogonal deprotection of the carbamate protection group is achieved at a temperature of less than about 55° C., such as less than about 50° C., such as less than about 40° C., such as less than about 30° C., such as at or about 25° C. or at room temperature. In some embodiments orthogonal deprotection of the carbamate protection group is achieved in a period of less than about 4 hours at a temperature of less than about 55° C., such as less than about 50° C., such as less than about 40° C., such as less than about 30° C., such as at or about 25° C. or at room temperature. In some embodiments orthogonal deprotection of the carbamate protection group is achieved in a period of less than about 2 hours at a temperature of less than about 55° C., such as less than about 50° C., such as less than about 40° C., such as less than about 30° C., such as at or about 25° C. or at room temperature. In some embodiments orthogonal deprotection of the carbamate protection group is achieved in a period of about 1 hour at a temperature of less than about 55° C., such as less than about 50° C., such as less than about 40° C., such as less than about 30° C., such as at or about 25° C. or at room temperature.

1 Pot Process

In some embodiments, the carbamate protection group removal is performed (occurs) during global deprotection and cleavage of the oligonucleotide from the solid support, referred to herein as the 1 pot process. Global deprotection and cleavage may use the standard procedures used in phosphoramidite oligonucleotide synthesis, such as with ammonium hydroxide at about 55° C. to about 60° C. Typically concentrated ammonium hydroxide is used (~28-35%) defined by saturation limit of $NH_3$ in water.

Two Pot Process

In some embodiments, the carbamate protection group is removed prior to global deprotection (orthogonal deprotection). The selective removal of the carbamate protection group is typically achieved by treatment with a suitable base in an organic solvent, for example 20% Diethylamine in acetonitrile, or 20% piperidine in dimethylformamide. However, for e.g. silyl carbamates, may be achieved via treatment with a fluoride ion, typically in the form of tetrabutylammonium fluoride in the solvent tetrahydrofuran.

The carbamate protection group used in the two-pot or three-pot process (and optionally the 1 pot process), is an orthogonal protection group which may be specifically removed (deprotected) with or without removal of the chiral auxiliary, but without global deprotection/cleavage from the solid support.

The reagent used for removal of the carbamate protection group may be optimized for each specific carbamate group. Examples include treatment with 20% piperidine in N,N-dimethylformamide (e.g. for Fmoc) or 20% triethylamine or diethylamine in acetonitrile (e.g. for cyanoethyl carbamate), or 1M tetrabutyl fluoride in tetrahydrofuran (this is for Si-containing protecting group).

For example, when the carbamate protection group is Fmoc, the Fmoc protection group may be orthogonally removed from the nitrogen of the chiral auxiliary by reaction with a piperidine solution, such as 20% piperidine in DMF, which may for example be used at room temperature for 1 hour.

Alternatively, when the carbamate protection group is a cyano-ethyl carbamate, it may be orthogonally removed using an amine wash, as described herein (see also for example, U.S. Pat. No. 7,186,822). One preferred reagent for removal of orthogonal protection groups, such as cyano-ethyl is triethylamine in acetonitrile (1:1, v/v), e.g. at 25° C. or 10% diethylamine in acetonitrile, e.g. at 25° C.

In some embodiments orthogonal deprotection of the carbamate protection group is achieved at a temperature of less than about 55° C., such as less than about 50° C., such as less than about 40° C., such as less than about 30° C., such as at or about 25° C. or at room temperature.

Subsequent to orthogonal removal of the carbamate protection group, the oligonucleotide may undergo a global deprotection, cleavage of the chiral auxiliary and cleavage from the solid support (referred to as a 2 pot process). The first step (pot 1) being orthogonal deprotection of the carbamate protection group from the amine of the chiral auxiliary, followed by the second step (pot 2), of global deprotection. Global deprotection and cleavage may use the standard procedure used in phosphoramidite oligonucleotide synthesis, such as with ammonium hydroxide at 55°.

Three Pot Process

In some embodiments, after orthogonal removal of the carbamate protection group, and prior to global deprotection and cleavage from the solid support, a step of cleavage of the chiral auxiliary is performed. Selected removal of the chiral auxiliary, may be performed by treatment with DBU (1,8-Diazabicyclo(5.4.0)undec-7-ene), for example which may be used for 1 hour at room temperature. The three pot process comprises the first step (pot 1) of orthogonal deprotection of the carbamate protection group from the amine of the chiral auxiliary, followed by the second step (pot 2), of removal of the chiral auxiliary group(s), followed by a third step (pot 3) of global deprotection and cleavage from the solid support.

The use of the 2 pot or three pot process allows for a more rapid deprotection, and cleavage process, which can be performed at a lower temperature, and may result in improved oligonucleotide purity/quality. The orthogonal protection process (2 pot and 3 pot process) are therefore beneficial as compared to the non-orthogonal process of the prior art process using a trifolouroacetyl amine protection group.

3'-LNA Oligonucleotides

In some embodiments, the oligonucleotide synthesized by the method of the invention is an LNA oligonucleotide. In some embodiments the 3' terminal nucleoside of the oligonucleotide of the invention is an LNA oligonucleotide. As shown in the examples, the present inventors have discovered that LNA oligonucleotides with a 3' terminal LNA bound to the solid support (e.g. a support containing a UnyLinker moiety, as disclosed herein), can be cleaved from the Unylinker moiety of the solid support under conditions for global deprotection and cleavage in about 1-about 4 hours (e.g. ammonium hydroxide at about 55° C.-about 60° C.). Indeed within about 4 hours of global deprotection, LNA oligonucleotides with a 3' LNA nucleoside, such as a LNA with a 2'-O—CH$_2$-4' bridge, can be effectively cleaved and deprotected from a UnyLinker solid support.

Activators

Activators are reagents used prior to or during the coupling step of oligonucleotide synthesis which activate the phosphoramidite monomer to allow coupling of the monomer to the 5' terminal group attached to the solid support or oligonucleotide chain.

In some embodiments, the activator comprises N-methylimidazole. In some embodiments, the activator comprises 4,5-dicyanoimidazole (DCI), tetrazole, or 5-(Benzylthio)-1H-tetrazole. In some embodiments, the activator comprises 4,5-dicyanoimidazole (DCI), tetrazole, or 5-(Benzylthio)-1H-tetrazole and N-methylimidazole.

As disclosed herein, in some embodiments, the coupling reaction (i) is performed in an acetonitrile solution, optionally comprising an aromatic heterocyclic solvent, and the activator. In some embodiments the aromatic heterocyclic solvent is pyridine.

In some embodiments, the concentration of N-methylimidazole used is 0.01M-about 1M N-methylimidazole, such as about 0.1M N-methylimidazole. In some embodiments, the acetonitrile solution comprises N-methylimidazole in a concentration of 0.01M-about 1M N-methylimidazole, such as about 0.1M N-methylimidazole.

In some embodiments, the activator is DCI or tetrazole, or 5-(Benzylthio)-1H-tetrazole, which may be used at a concentration (e.g. in the acetonitrile solution) of about 0.5-about 2M, such as about 1M.

Stereodefined Phosphorothioate Oligonucleotides

Typically, oligonucleotide phosphorothioates are synthesised as a random mixture of Rp and Sp phosphorothioate linkages (also referred to as a diastereomeric mixture). In the method of the present invention, phosphorothioate oligonucleotides are provided where at least one of the phosphorothioate linkages of the oligonucleotide is stereodefined, i.e. is either Rp or Sp in at least 75%, such as at least 80%, or at least 85%, or at least 90% or at least 95%, or at least 97%, such as at least 98%, such as at least 99%, or (essentially) all of the oligonucleotide molecules present in the oligonucleotide sample. Stereodefined oligonucleotides comprise at least one phosphorothioate linkage which is stereodefined. The term stereodefined, may be used to describe a defined chirality of one or more phosphorothioate internucleoside linkages as either Rp or Sp, or may be used to described a oligonucleotide which comprises such a (or more) phosphorothioate internucleoside linkage. It is recognised that a stereodefined oligonucleotide may comprise a small amount of the alternative stereoisomer at any one position, for example Wan et al reports a 98% stereoselectivity for the gapmers reported in NAR, November 2014.

LNA Oligonucleotide

An LNA oligonucleotide is an oligonucleotide which comprises at least one LNA nucleoside. The LNA oligonucleotide may be an antisense oligonucleotide.

The term oligonucleotide as used herein is defined as it is generally understood by the skilled person as a molecule comprising two or more covalently linked nucleosides. For use as an antisense oligonucleotide, oligonucleotides are typically synthesised as 7-30 nucleotides in length.

The term "antisense oligonucleotide" as used herein is refers to oligonucleotides capable of modulating expression of a target gene by hybridizing to a target nucleic acid, in particular to a contiguous sequence on a target nucleic acid. An antisense oligonucleotide can also be defined by it's complementary to a target nucleic acid. Antisense oligonucleotides are single stranded. Antisense oligonucleotides are not essentially double stranded and are not therefore siRNAs. An antisense oligonucleotide comprises a contiguous nucleotide which is complementary to a target nucleic acid. Antisense oligonucleotides typically comprise one or more modified internucleoside linkages, and may by way of a non-limiting example be in the form of a a LNA gapmer or a mixed wing gapmer. In other embodiments the oligonucleotide may be an LNA mixmers (LNA and non-LNA nucleotides, e.g. LNA and DNA (see e.g. WO2007/112754 hereby incorporated by reference), or LNA and 2'-O-MOE nucleotides, or LNA, DNA and 2'O-MOE nucleotides), or a LNA totalmers (only LNA nucleotides—see. E.g. WO2009/043353 hereby incorporated by reference).

The term "modified internucleoside linkage" is defined as generally understood by the skilled person as linkages other than phosphodiester (PO) linkages, that covalently couples two nucleosides together. Modified internucleoside linkages are particularly useful in stabilizing oligonucleotides for in vivo use, and may serve to protect against nuclease cleavage. A phosphorothioate internucleoside linkage is particularly useful due to nuclease resistance, beneficial pharmakokinetics and ease of manufacture. In some embodiments at least 70%, such as at least 80 or such as at least 90% of the internucleoside linkages in the oligonucleotide, or contiguous nucleotide sequence thereof, are phosphorothioate. In some embodiments all of the internucleoside linkages of the oligonucleotide, or contiguous nucleotide sequence thereof, are phosphorothioate, wherein at least one of the phosphorothioate internucleoside linkages is a stereodefined phosphorothioate internucleoside linkage (originating from the incorporation of the oxazaphospholidine phosphoramidite monomer into the oligonucleotide during oligonucleotide synthesis). Further internucleoside linkers are disclosed in WO2009/124238 (incorporated herein by reference).

The term nucleobase includes the purine (e.g. adenine and guanine) and pyrimidine (e.g. uracil, thymine and cytosine) moiety present in nucleosides and nucleotides which form hydrogen bonds in nucleic acid hybridization. In the context of the present invention the term nucleobase also encompasses modified nucleobases which may differ from naturally occurring nucleobases, but are functional during nucleic acid hybridization. In some embodiments the nucleobase moiety is modified by modifying or replacing the nucleobase. In this context "nucleobase" refers to both naturally occurring nucleobases such as adenine, guanine, cytosine, thymidine, uracil, xanthine and hypoxanthine, as well as non-naturally occurring variants. Such variants are for example described in Hirao et al (2012) Accounts of Chemical Research vol 45 page 2055 and Bergstrom (2009) Current Protocols in Nucleic Acid Chemistry Suppl. 37 1.4.1.

Nucleotides are the building blocks of oligonucleotides and polynucleotides, and for the purposes of the present invention include both naturally occurring and non-naturally occurring nucleotides. In nature, nucleotides, such as DNA and RNA nucleotides comprise a ribose sugar moiety, a nucleobase moiety and one or more phosphate groups (which is absent in nucleosides). Modified nucleosides and nucleotides are modified as compared to the equivalent DNA or RNA nucleoside/tide by the introduction of a modification to the ribose sugar moiety, the nucleobase moiety, or in the case of modified nucleotides, the internucleoside linkage. Nucleosides and nucleotides may also interchangeably be referred to as "units" or "monomers".

The term "modified nucleoside" or "nucleoside modification" as used herein refers to nucleosides modified as compared to the equivalent DNA or RNA nucleoside by the introduction of one or more modifications of the sugar moiety or the (nucleo)base moiety. The term modified nucleoside may also be used herein interchangeably with the term "nucleoside analogue" or modified "units" or modified "monomers". Examples of modified nucleosides are described in the separate section "Oligomer modifications" and its sub-sections.

Locked Nucleic Acid Nucleosides (LNA).

LNA nucleosides are modified nucleosides which comprise a linker group (referred to as a biradicle or a bridge) between C2' and C4' of the ribose sugar ring of a nucleotide (i.e. the embodiment where $R^2$ and $R^4$ together designate a bivalent bridge).

These nucleosides are also termed bridged nucleic acid or bicyclic nucleic acid (BNA) in the literature.

In some embodiments, the oxazaphospholidine phosphoramidite monomer is or comprises a LNA nucleoside, for example the monomer may be of formula 17 or formula 18

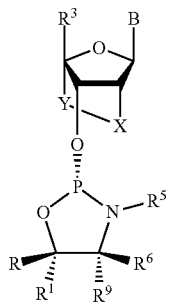

Formula 17

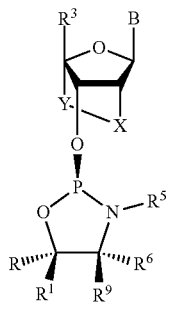

Formula 18

Wherein B designates the nucleobase; R, $R^1$, $R^6$, $R^3$, $R^9$, $R^5$ are as according to formula A, A(i), A(ii) or any one of formulas 1, 2, 3, 4, 5, 6, 7, 8, 9, 10, 11, 12, 13, 14, 15 or 16.

In some embodiments of formula 17, B is other than DMF protected guanine. In some embodiments B is either adenine or thymine. In some embodiments B is DMF protected adenine.

X designates a group selected from the list consisting of —C($R^aR^b$)—, —C($R^a$)=C($R^b$)—, —C($R^a$)=N—, —O—, —Si($R^a$)$_2$—, —S—, —SO$_2$—, —N($R^a$)—, and >C=Z In some embodiments, X is selected from the group consisting of: —O—, —S—, NH—, N$R^aR^b$, —CH$_2$—, C$R^aR^b$, —C(=CH$_2$)—, and —C(=C$R^aR^b$)—

In some embodiments, X is —O—

Y designates a group selected from the group consisting of —C($R^aR^b$)—, —C($R^a$)=C($R^b$)—, —C($R^a$)=N—, —O—, —Si($R^a$)$_2$—, —S—, —SO$_2$—, —N($R^a$)—, and >C=Z In some embodiments, Y is selected from the group consisting of: —CH$_2$—, —C($R^aR^b$)—, —CH$_2$CH$_2$—, —C($R^aR^b$)—C($R^aR^b$)—, —CH$_2$CH$_2$CH$_2$—, —C($R^aR^b$)C($R^aR^b$)C($R^aR^b$)—, —C($R^a$)=C($R^b$)—, and —C($R^a$)=N—

In some embodiments, Y is selected from the group consisting of: —CH$_2$—, —CH$R^a$—, —CHCH$_3$—, —C$R^aR^b$— or —X—Y— together designate a bivalent linker group (also referred to as a radicle) together designate a bivalent linker group consisting of 1, 2, or 3 groups/atoms selected from the group consisting of —C($R^aR^b$)—, —C($R^a$)=C($R^b$)—, —C($R^a$)=N—, —O—, —Si($R^a$)$_2$—, —S—, —SO$_2$—, —N($R^a$)—, and >C=Z, In some embodiments, —X—Y— designates a biradicle selected from the groups consisting of: —X—CH$_2$—, —X—C$R^aR^b$—, —X—CH$R^a$—, —X—C(HCH$_3$)—, —O—Y—, —O—CH$_2$—, —S—CH$_2$—, —NH—CH$_2$—, —CH$_2$—O—CH$_2$—, —O—CH(CH$_3$CH$_3$)—, —O—CH$_2$—CH$_2$—, OCH$_2$—CH$_2$—CH$_2$—, —O—CH$_2$OCH$_2$—, —O—NCH$_2$—, —C(=CH$_2$)—CH$_2$—, —N$R^a$—CH$_2$—, N—O—CH$_2$, —S—C$R^aR^b$— and —S—CHR$^a$—.

In some embodiments —X—Y— designates —O—CH$_2$— or —O—CH(CH$_3$)—, and $R^a$ and, when present $R^b$, each is independently selected from hydrogen, optionally substituted C$_{1-6}$-alkyl, optionally substituted C$_{2-6}$-alkenyl, optionally substituted C$_{2-6}$-alkynyl, hydroxy, optionally substituted C$_{1-6}$-alkoxy, C$_{2-6}$-alkoxyalkyl, C$_{2-6}$-alkenyloxy, carboxy, C$_{1-6}$-alkoxycarbonyl, C$_{1-6}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di(C$_{1-6}$-alkyl)amino, carbamoyl, mono- and di(C$_{1-6}$-alkyl)-amino-carbonyl, amino-C$_{1-6}$-alkyl-aminocarbonyl, mono- and di(C$_{1-6}$-alkyl)amino-C$_{1-6}$-alkyl-aminocarbonyl, C$_{1-6}$-alkyl-carbonylamino, carbamido, C$_{1-6}$-alkanoyloxy, sulphono, C$_{1-6}$-alkylsulphonyloxy, nitro, azido, sulphanyl, C$_{1-6}$-alkylthio, halogen, where aryl and heteroaryl may be optionally substituted and where two geminal substituents $R^a$ and $R^b$ together may designate optionally substituted methylene (=CH$_2$), wherein for all chiral centers, asymmetric groups may be found in either R or S orientation.

$R^{10}$ may be hydrogen or in some embodiments may be selected from the group consisting of: optionally substituted C$_{1-6}$-alkyl, optionally substituted C$_{2-6}$-alkenyl, optionally substituted C$_{2-6}$-alkynyl, hydroxy, C$_{1-6}$-alkoxy, C$_{2-6}$-alkoxyalkyl, C$_{2-6}$-alkenyloxy, carboxy, C$_{1-6}$-alkoxycarbonyl, C$_{1-6}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di(C$_{1-6}$-alkyl)amino, carbamoyl, mono- and di(C$_{1-6}$-alkyl)-amino-carbonyl, amino-C$_{1-6}$-alkyl-aminocarbonyl, mono- and di(C$_{1-6}$-alkyl)amino-C$_{1-6}$-alkyl-aminocarbonyl, C$_{1-6}$-alkyl-carbonylamino, carbamido, C$_{1-6}$-alkanoyloxy, sulphono, C$_{1-6}$-alkylsulphonyloxy, nitro, azido, sulphanyl, C$_{1-6}$-alkylthio, halogen, where aryl and heteroaryl may be optionally substituted, and where two geminal substituents together may designate oxo, thioxo, imino, or optionally substituted methylene.

In some embodiments $R^{10}$ is selected from C$_{1-6}$ alkyl, such as methyl, and hydrogen.

In some embodiments $R^{10}$ is hydrogen.

In some embodiments, $R^a$ is either hydrogen or methyl. In some embodiments, when present, $R^b$ is either hydrogen or methyl.

In some embodiments, one or both of $R^a$ and $R^b$ is hydrogen

In some embodiments, one of $R^a$ and $R^b$ is hydrogen and the other is other than hydrogen In some embodiments, one of $R^a$ and $R^b$ is methyl and the other is hydrogen In some embodiments, both of $R^a$ and $R^b$ are methyl.

In some embodiments, the biradicle —X—Y— is —O—CH$_2$—, and $R^{10}$ is hydrogen. In some embodiments, the biradicle —X—Y— is —S—CH$_2$—, and $R^{10}$ is hydrogen.

In some embodiments, the biradicle —X—Y— is —NH—CH$_2$—, and $R^{10}$ is hydrogen.

In some embodiments, the biradicle —X—Y— is —O—CH$_2$—CH$_2$— or —O—CH$_2$—CH$_2$—CH$_2$—, and $R^{10}$ is hydrogen.

In some embodiments, the biradicle —X—Y— is —O—CH$_2$—, and $R^{10}$ is C$_{1-6}$ alkyl, such as methyl.

In some embodiments, the biradicle —X—Y— is —O—CR$^a$R$^b$—, wherein one or both of $R^a$ and $R^b$ are other than hydrogen, such as methyl, and $R^{10}$ is C$_{1-6}$ alkyl, such as methyl. In some embodiments, the biradicle —X—Y— designate the bivalent linker group —O—CH(CH$_2$OCH$_3$)— (2' O-methoxyethyl bicyclic nucleic acid— Seth at al., 2010, J. Org. Chem., 2010, 75 (5), pp 1569-1581). In some embodiments, the biradicle —X—Y— designate the bivalent linker group —O—CH(CH$_2$CH$_3$)— (2'O-ethyl bicyclic nucleic acid— Seth at al., 2010, J. Org. Chem). In some embodiments, the biradicle —X—Y— is —O—CHR$^a$—, and $R^{10}$ is hydrogen.

In some embodiments, the biradicle —X—Y— is —O—CH(CH$_2$OCH$_3$)—, and $R^{10}$ is hydrogen. Such LNA nucleosides are also known as cyclic MOEs in the art (cMOE) and are disclosed in WO07090071.

In some embodiments, the biradicle —X—Y— designate the bivalent linker group —O—CH(CH$_3$)— in either the R- or S-configuration. In some embodiments, the biradicle —X—Y— together designate the bivalent linker group —O—CH$_2$—O—CH$_2$— (Seth at al., 2010, J. Org. Chem). In some embodiments, the biradicle —X—Y— is —O—CH(CH$_3$)—, and $R^{10}$ is hydrogen. Such 6' methyl LNA nucleosides are also known as cET nucleosides in the art, and may be either (S)cET or (R)cET stereoisomers, as disclosed in WO07090071 (beta-D) and WO2010/036698 (alpha-L).

In some embodiments, the biradicle —X—Y— is —O—CR$^a$R$^b$—, wherein in neither $R^a$ or $R^b$ is hydrogen, and $R^{10}$ is hydrogen. In some embodiments, $R^a$ and $R^b$ are both methyl.

In some embodiments, the biradicle —X—Y— is —S—CHR$^a$—, and $R^{10}$ is hydrogen.

In some embodiments, the biradicle —X—Y— is —C(=CH$_2$)—C(R$^a$R$^b$)—, such as —C(=CH$_2$)—CH$_2$—, or —C(=CH$_2$)—CH(CH$_3$)—, and $R^{10}$ is hydrogen.

In some embodiments the biradicle —X—Y— is —N(—OR$^a$)—, and $R^{10}$ is hydrogen. In some embodiments $R^a$ is C$_{1-6}$ alkyl such as methyl. In some embodiments, the biradicle —X—Y— together designate the bivalent linker group —O—NR$^a$—CH$_3$— (Seth at al., 2010, J. Org. Chem). In some embodiments the biradicle —X—Y— is —N(R$^a$)—, and $R^{10}$ is hydrogen. In some embodiments $R^a$ is C$_{1-6}$ alkyl such as methyl.

In some embodiments, and $R^{10}$ is C$_{1-6}$ alkyl such as methyl. In such an embodiment, the biradicle —X—Y— may be selected from —O—CH$_2$— or —O—C(HCR$^a$)—, such as —O—C(HCH$_3$)—.

In some embodiments, the biradicle is —CR$^a$R$^b$—O—CR$^a$R$^b$—, such as CH$_2$—O—CH$_2$—, and $R^{10}$ is hydrogen. In some embodiments $R^a$ is C$_{1-6}$ alkyl such as methyl.

In some embodiments, the biradicle is —O—CR$^a$R$^b$—O—CR$^a$R$^b$—, such as O—CH$_2$—O—CH$_2$—, and $R^{10}$ is hydrogen. In some embodiments $R^a$ is C$_{1-6}$ alkyl such as methyl.

It will be recognized than, unless specified, the LNA nucleosides may be in the beta-D or alpha-L stereoisoform.

As illustrated in the examples, in some embodiments of the invention the LNA nucleosides are or comprise beta-D-oxy-LNA nucleosides, such as where the 2'-4' bridge is as per formula I, and where X is oxygen, Y is CH$_2$, and $R^{10}$ is hydrogen.

DNA Nucleosides

In some embodiments, the oxazaphospholidine phosphoramidite monomer is or comprises a DNA nucleoside, for example the monomer may be of formula 19 or formula 20:

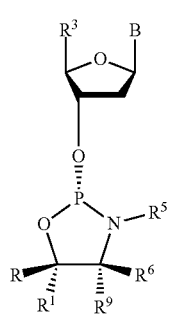

Formula 19

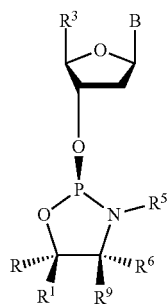

Formula 20

Wherein B designates the nucleobase; R, $R^1$, $R^6$, $R^3$, $R^9$, $R^5$ are as according to formula A, A(i), A(ii) or any one of formulas 1, 2, 3, 4, 5, 6, 7, 8, 9, 10, 11, 12, 13, 14, 15 or 16. In some embodiments of formula 20, B is adenine, such as protected adenine, such as Bz protected adenine.

In some embodiments, the oxazaphospholidine phosphoramidite monomer is as according to formula 21 and 22:

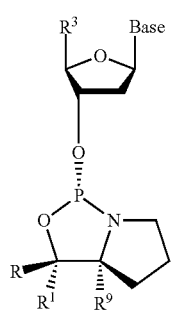

formula 21

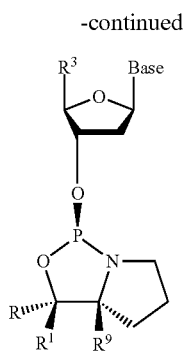

formula 22

Wherein Base designates the nucleobase; R, $R^1$, $R^3$, $R^9$, are as according to formula A, A(i), A(ii) or any one of formulas 1, 2, 3, 4, 5, 6, 7, 8, 9, 10, 11, 12, 13, 14, 15 or 16. In some embodiments of formula 20 or 22, B is adenine, such as protected adenine, such as Bz protected adenine. In some embodiments of the monomer of formula 19, 20, 21, or 22, R is phenyl, and $R^1$ is either hydrogen or methyl. In some embodiments of the monomer of formula 19, 20, 21 or 22, $R^3$ is $CH_2$—O-DMTr or $CH_2$—O-MMTr.

Oligonucleotides Comprising DNA and/or Affinity Enhancing Nucleosides

In some embodiments, the oligonucleotide is a DNA phosphorothioate oligonucleotide. DNA phosphorothioate oligonucleotides comprise only DNA nucleosides, and in some embodiments may comprise only stereodefined phosphorothioate internucleoside linkages. DNA phosphorothioates may for example be 18-25 nucleotides in length.

In some embodiments, the oligonucleotide comprises one or more affinity enhancing nucleosides, such as LNA or 2' substituted nucleosides described herein. Affinity enhancing nucleosides, such as 2'-O-MOE or 2'-Omethyl are often used in antisense oligonucleotides, either in combination with other nucleosides, such as DNA nucleosides, in the form of, e.g. mixmers or gapmers, or may be used in fully sugar modified oligonucleotides, where all of the nucleosides are other than DNA or RNA.

In some embodiments the oligonucleotide synthesised by the process or method of the invention may be a gapmer, and LNA gapmer, or a mixed wing gapmer.

Gapmer

The term gapmer as used herein refers to an antisense oligonucleotide which comprises a region of RNase H recruiting oligonucleotides (gap) which is flanked 5' and 3' by one or more affinity enhancing modified nucleosides (flanks). Various gapmer designs are described herein. Headmers and tailmers are oligonucleotides capable of recruiting RNase H where one of the flanks are missing, i.e. only one of the ends of the oligonucleotide comprises affinity enhancing modified nucleosides. For headmers the 3' flank is missing (i.e. the 5' flank comprise affinity enhancing modified nucleosides) and for tailmers the 5' flank is missing (i.e. the 3' flank comprises affinity enhancing modified nucleosides).

LNA Gapmer

The term LNA gapmer is a gapmer oligonucleotide wherein at least one of the affinity enhancing modified nucleosides is an LNA nucleoside.

Mixed Wing Gapmer

The term mixed wing gapmer refers to a LNA gapmer wherein the flank regions comprise at least one LNA nucleoside and at least one non-LNA modified nucleoside, such as at least one 2' substituted modified nucleoside, such as, for example, 2'-O-alkyl-RNA, 2'-O-methyl-RNA, 2'-alkoxy-RNA, 2'-O-methoxyethyl-RNA (MOE), 2'-amino-DNA, 2'-Fluoro-DNA, arabino nucleic acid (ANA), 2'-fluoro-ANA and 2'-F-ANA nucleoside(s). In some embodiments the mixed wing gapmer has one flank which comprises LNA nucleosides (e.g. 5' or 3') and the other flank (3' or 5' respectfully) comprises 2' substituted modified nucleoside(s).

Length

When referring to the length of a nucleotide molecule as referred to herein, the length corresponds to the number of monomer units, i.e. nucleotides, irrespective as to whether those monomer units are nucleotides or nucleotide analogues. With respect to nucleotides, the terms monomer and unit are used interchangeably herein.

The process of the present invention is particularly suitable for the purification of short oligonucleotides, for example, consisting of 7 to 30 nucleotides, such as 7-10, such as 7, 8, 9, 10 or 10 to 20 nucleotides, such as 12 to 18 nucleotides, for example, 12, 13, 14, 15, 16, 17 or 18 nucleotides.

EXAMPLES

We have previously illustrated that L-LNA-G monomers where the G residue is acyl protected have greatly increased solubility and stability in coupling solvents—see EP 16161089.4 which is hereby incorporated by reference. Examples 1-6 of EP 16161089.4 are hereby directly incorporated by reference in their entirety.

We have previously illustrated that the addition of an aromatic heterocyclic solvent to the coupling solvent used in step (i) greatly enhances coupling efficacy—see EP 16169429.4 which is hereby incorporated by reference. Examples 1-12 of EP 16169429.4 are hereby directly incorporated by reference in their entirety.

Example 1

A 1 μmole scale synthesis was carried out using T-succinate loaded CPG solid support. Using conventional 5'-dimethoxytrityl-3'-β-cyanoethyl deoxythymidine phosphoramidite, 9 stereorandom couplings were carried out, followed by one stereodefined coupling, using a deoxythymidine phosphoramidite of the formula 23 followed by 5 stereorandom couplings again with 5'-dimethoxytrityl-3'-β-cyanoethyl deoxythymidine phosphoramidite. All synthetic steps are carried out according to the cycle depicted in FIG. 1, with the reagents listed below. In the single stereodefined coupling, a solution of 0.5M 9-Fluorenylmethyl N-succinimidyl carbonate in dichloromethane was mixed with a solution of 0.5M Diisopropylethylamine on the synthesizer in various ratios (as indicated in FIG. 4) after the sulphurization step, but prior to the capping step. The solid support was hereafter mixed with 1 mL concentrated ammonium hydroxide, and left for 1 h at 55° C., followed by evaporation in vacuo.

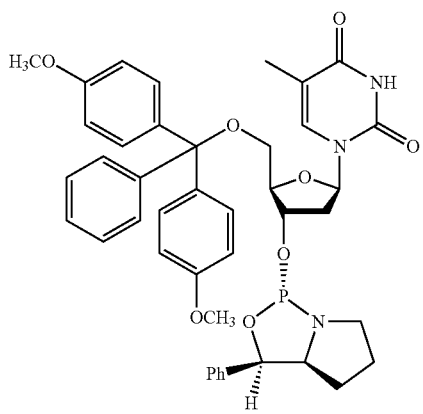

Formula 23

Reagents used in the synthetic cycle:

| | |
|---|---|
| Deblock | 3% Dichloroacetic acid in dichloromethane (v/v) |
| Activator | 1M Dicyanoimidazole and 0.1M N-methylimidazole in acetonitrile |
| Cap A | 20% 1-Methylimidazol in acetonitrile (v/v) |
| Cap B1 | 40% Acetic acid anhydride in acetonitrile (v/v) |
| Cap B2 | 60% Pyridine or 2,6-lutidine in acetonitrile (v/v) |
| Sulfurizing reagent | 0.1M Xanthane hydride in 1 |

In the bottom chromatogram the synthesis was carried out similar to above, but with no Fmoc protection. It is seen, in this case, that there is a large peak corresponding to the product containing the N-acetylated chiral auxiliary. If Fmoc protection is introduced before capping, this peak has virtually disappeared, indicating that Fmoc protection is highly effective, and induced very rapid cleavage of the chiral auxiliary from the oligonucleotide. See FIG. 4.

Example 2: Comparison of Synthesis of Fully Stereodefined Oligonucleotide with and without Fmoc Protection Prior to Capping A 1 μmole synthesis of the following fully stereodefined oligonucleotide was carried out using phosphoramidites of the structure from formula 23

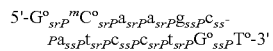

Wherein uppercase letters denote LNA nucleotides, and lowercase letters denote DNA nucleotides, with the stereoconfiguration of the internucleotidic phosphorthioate indicated between the two relevant nucleotides. "srP" denotes R-configured phosphorthioate, "ssP" denotes S-configured phosphorthioate.

The synthetic cycle used is the one depicted in FIG. 1, and the reagents are the same as in example 1

The results after 4 h deprotection are shown in FIG. 5.

The invention claimed is:

1. A method for the synthesis of a stereodefined phosphorothioate oligonucleotide, said method comprising the steps of (i) coupling a oxazapholidine chiral auxiliary phosphoramidite monomer to the 5' —OH group of a nucleoside, followed by the step (ii) of protecting the amine group of the oxazapholidine chiral auxiliary with a carbamate protection group, and (iii) sulfurization, wherein the sulfurization step (iii) is performed after the coupling step (i) and either prior to or subsequent to the amine protection step (ii).

2. The method according to claim 1, wherein the sulfurization step (iii) is performed prior to the amine protection step.

3. The method according to claim 1, wherein the sulfurization step (iii) is performed subsequent to the amine protection step.

4. The method according to claim 1, wherein the method further comprises a capping step (iv), which is performed subsequent to the amine protecting step (ii).

5. The method according to claim 4, wherein the capping step is performed prior to or subsequent to the sulfurization step (iv).

6. The method according to claim 1, wherein the oligonucleotide is synthesized on a solid support.

7. The method according to claim 6, wherein once chain elongation is complete, the amine carbamate protection group is removed during global oligonucleotide deprotection/cleavage from the solid support.

8. The method according to claim 6, wherein once chain elongation is complete, the amine carbamate protection group is removed prior to global deprotection/cleavage from the solid support.

9. The method according to claim 8, wherein after the amine carbamate protection group has been removed, the chiral auxiliary is removed prior to global deprotection/cleavage from the solid support.

10. The method according to claim 8, wherein after the amine carbamate protection group has been removed, the chiral auxiliary is removed during global deprotection/cleavage from the solid support.

11. The method according to claim 8, wherein the step of amine carbamate protection group removal is performed for less than 8 hours.

12. The method according to claim 1, wherein the step of amine carbamate protection group removal is performed at room temperature.

13. The method according to claim 1, wherein the oxazapholidine chiral auxiliary phosphoramidite monomer used in step i) is of formula A:

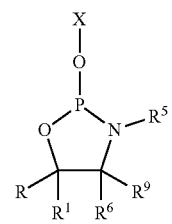

Formula A wherein X is the 3' oxygen of a nucleoside,
R$^1$ is selected from the groups consisting of hydrogen and C$_{1-3}$ alkyl; R$^9$ is hydrogen;
R is selected from the groups consisting of aryl, heteroaryl, substituted aryl, substituted heteroaryl, nitro, halogen, cyano, silyl, substituted silyl, sulfone, substituted sulfone, (aryl substituted sulfone), fluorene, and substituted fluorine;
R$^5$ and R$^6$ are independently selected from the group consisting of hydrogen, alkyl, cyclo-alkyl, aryl, heteroaryl, substituted alkyl, substituted cyclo-alkyl, substituted aryl, and substituted heteroaryl, or R$^5$ and R$^6$ together form a heterocyclic ring comprising 3-16 carbon atoms, together with the N atom of formula A.

14. The method according to claim 1, wherein the amine carbamate protection group is a substituted ethyl carbamate protection group of formula:

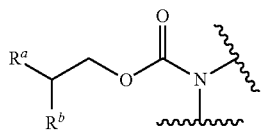

or

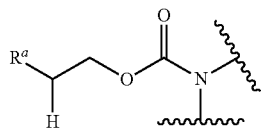

wherein N is the nitrogen present in the chiral auxiliary, and $R^a$, and optionally when present, $R^b$, is a group that allows for a deprotection of the carbamate protecting group via beta-elimination, said group independently selected from the group consisting of —CN, —SO$_2$R$^c$, —RiR$^c$$_3$, —F, —Cl, —CF$_3$, and —CO—R$^c$, wherein R$^c$ is independently selected from the group consisting of hydrogen, optionally substituted C$_{1-10}$ alkyl-, optionally substituted C$_{2-6}$ alkenyl-, optionally substituted C$_{2-6}$ alkynyl-, optionally substituted C$_{3-7}$ cycloalkyl-, optionally substituted C$_{1-10}$ alkyloxy or an aryl-group, or R$^b$ is selected from the group consisting of hydrogen, optionally substituted C$_{1-10}$ alkyl-, optionally substituted C$_{2-6}$ alkenyl-, optionally substituted C$_{2-6}$ alkynyl-, optionally substituted C$_{3-7}$ cycloalkyl-, optionally substituted C$_{1-10}$ alkyloxy or an aryl-group.

15. The method according to claim 1, wherein the amine carbamate protection group is an optionally substituted 2'-sulfonyl carbamate protection group of formula:

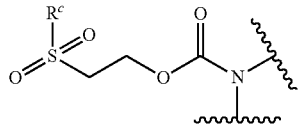

wherein N is the nitrogen present in the chiral auxiliary, and R$^c$ is independently selected from the group consisting of hydrogen, optionally substituted C$_{1-10}$ alkyl-, optionally substituted C$_{2-6}$ alkenyl-, optionally substituted C$_{2-6}$ alkynyl-, optionally substituted C$_{3-7}$ cycloalkyl-, optionally substituted C$_{1-10}$ alkyloxy or an aryl-group;

or R$^b$ is a group selected from the group consisting of hydrogen, optionally substituted C$_{1-10}$ alkyl-, optionally substituted C$_{2-6}$ alkenyl-, optionally substituted C$_{2-6}$ alkynyl-, optionally substituted C$_{3-7}$ cycloalkyl-, optionally substituted C$_{1-10}$ alkyloxy or an aryl-group.

16. The method according to claim 1, wherein the amine carbamate protection group is selected from the group consisting of

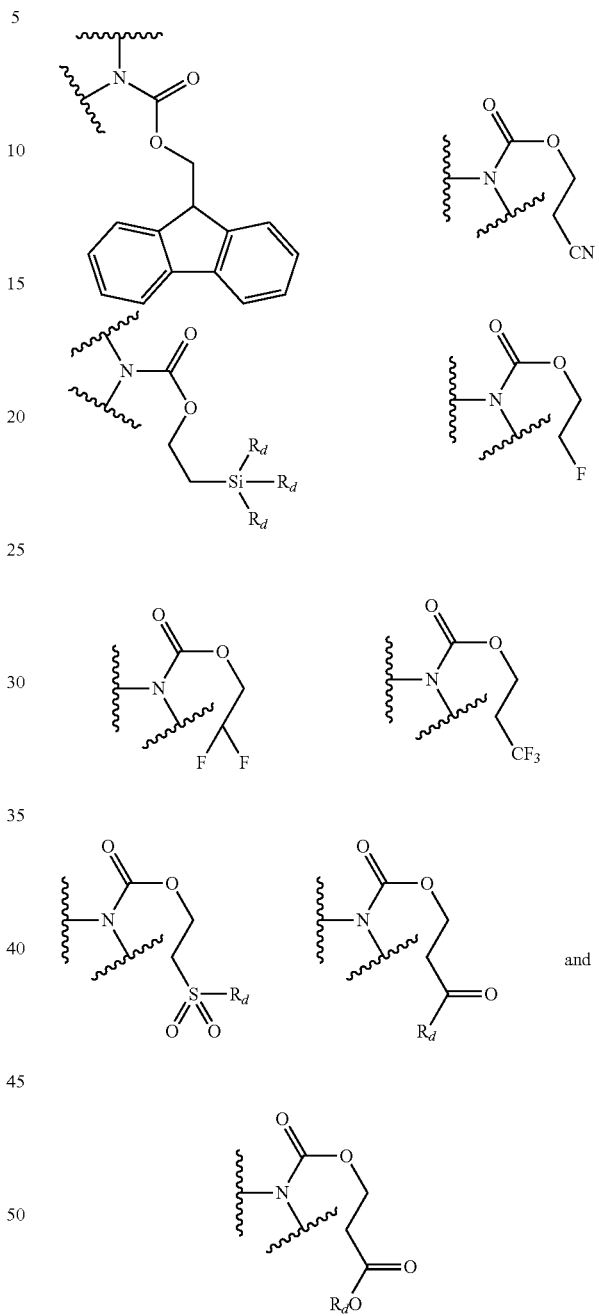

and wherein the N is the N present in the chiral auxiliary, and R$_d$ is selected from the group consisting of hydrogen, optionally substituted C$_{1-10}$ alkyl-, optionally substituted C$_{2-6}$ alkenyl-, optionally substituted C$_{2-6}$ alkynyl-, optionally substituted C$_{3-7}$ cycloalkyl-, optionally substituted C$_{1-10}$ alkyloxy or an aryl-group.

17. The method according to claim 1, wherein step (ii) comprises reacting a carbamate precursor and the coupled an amine containing chiral auxiliary phosphoramidite monomer provided in step (i), under conditions to allow the substitution of the nitrogen of the chiral auxiliary with the carbamate protection group.

18. The method according to claim 17, wherein the carbamate precursor is selected from the group consisting of

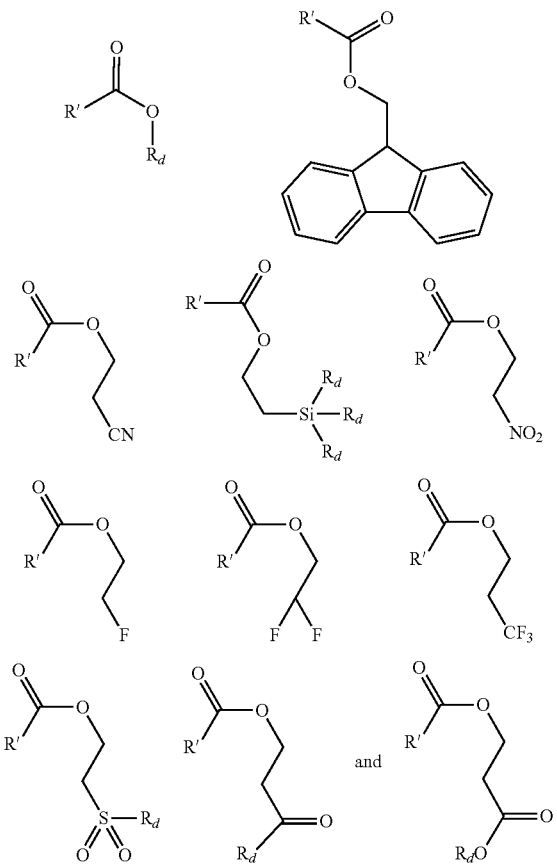

where in $R_d$ is selected from the group consisting hydrogen, optionally substituted $C_1$-10 alkyl-, optionally substituted $C_{2-6}$ alkenyl-, optionally substituted $C_{2-6}$ alkynyl-, optionally substituted $C_{3-7}$ cycloalkyl-, optionally substituted $C_{1-10}$ alkyloxy or an aryl-group, and R' is a leaving group selected from the group consisting of

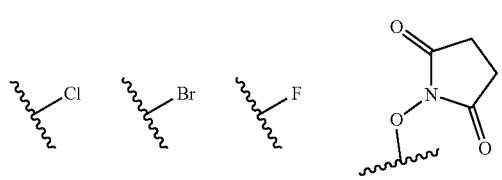

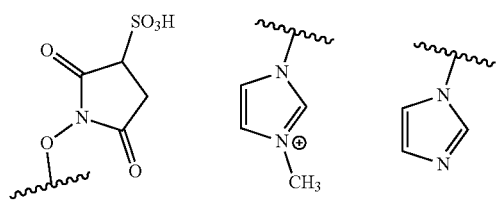

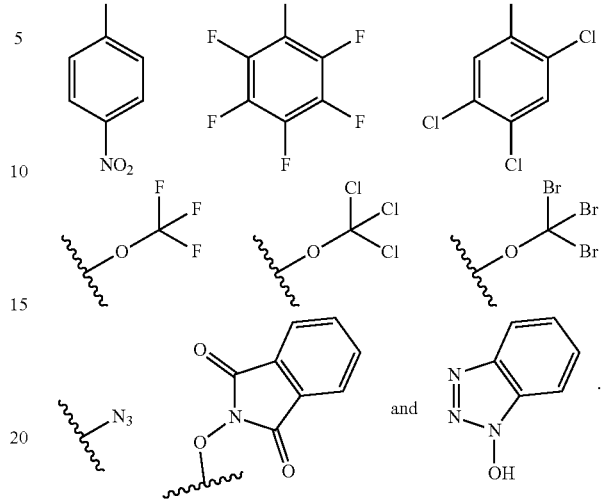

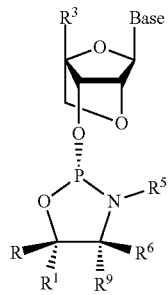

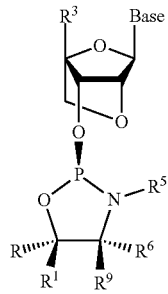

and

19. The method according to claim 17, wherein $R^4$ and $R^2$ are hydrogen.

20. The method according to claim 17, wherein the chiral auxiliary phosphoramidite monomer is of formula 3 or 4, Formula 3

Formula 4 wherein Base is a nucleobase;

$R^5$ and $R^6$ are independently selected from the group consisting of hydrogen, alkyl, cyclo-alkyl, aryl, heteroaryl, substituted alkyl, substituted cyclo-alkyl, substituted aryl, and substituted heteroaryl, or $R^5$ and $R^6$ together form a heterocyclic ring comprising 3-16 carbon atoms;

$R^1$ is selected from the groups consisting of hydrogen and $C_{1-3}$ alkyl; $R^9$ is hydrogen;

R is selected from the groups consisting of aryl, heteroaryl, substituted aryl, substituted heteroaryl, nitro, halogen, cyano, silyl, substituted silyl, sulfone, substituted sulfone (aryl substituted sulfone), fluorene, and substituted fluorine;

R³ is selected from the group consisting of CH₂ODMTr, CH₂-Alkyl-O-DMTr, CH-Me-O-DMTr, CH₂OMMTr, CH₂-Alkyl-O-MMTr, CH(Me)-O-MMTr, CH—R$^a$—O-DMTrR$^b$, and CH—R$^a$—O-MMTrR$^b$;

R² is selected from the groups consisting of halo, such as —F, amino, azido, —SH, —CN, —OCN, —CF₃, —OCF₃, —O(R$_m$)-alkyl, —S(R$_m$)-alkyl, —N(R$_m$)-alkyl, —O(R$_m$)-alkenyl, —S(R$_m$)-alkenyl, —N(R$_m$)-alkenyl; —O(R$_m$)-alkynyl, —S(R$_m$)-alkynyl or —N(R$_m$)-alkynyl; O-alkylenyl-O-alkyl, alkynyl, alkaryl, aralkyl, O-alkaryl, O-aralkyl, O(CH₂)₂SCH₃, O—(CH₂)₂—O—N(R$_m$)(R$_n$) or O—CH₂C(=O)—N(R$_m$)(R$_n$), —O—(CH₂)₂OCH3, and —O—CH₃, where each R$_m$ and R$_n$ are independently, H, an amino protecting group or substituted or unsubstituted C$_{1-10}$ alkyl;

R⁴ is selected from the group consisting of alkyl, cyclo-alkyl, cyclo-heteroalkyl, O-alkyl, S-alkyl, NH-alkyl, and hydrogen;

or R² and R⁴ together designate a bivalent bridge consisting of 1, 2, 3 groups/atoms selected from the group consisting of —C(R$^a$R$^b$)—, —C(R$^a$)=C(R$^b$), —C(R$^a$)=N, O, —Si(R$^a$)₂—, S—, —SO₂—, —N(R$^a$)—, and >C=Z;

wherein IV and, when present R$^b$, each is independently selected from hydrogen, optionally substituted C$_{1-6}$-alkyl, optionally substituted C$_{2-6}$-alkenyl, optionally substituted C$_{2-6}$-alkynyl, hydroxy, optionally substituted C$_{1-6}$-alkoxy, C₂ alkoxyalkyl, C$_{2-6}$-alkenyloxy, carboxy, C$_{1-6}$-alkoxycarbonyl, C$_{1-6}$-alkylcarbonyl, formyl, aryl, aryl-oxy-carbonyl, aryloxy, arylcarbonyl, heteroaryl, hetero-aryloxy-carbonyl, heteroaryloxy, heteroarylcarbonyl, amino, mono- and di(C$_{1-6}$-alkyl)amino, carbamoyl, mono- and di(C$_{1-6}$-alkyl)-aminocarbonyl, amino-C$_{1-6}$-alkyl-aminocarbonyl, mono- and di(C$_{1-6}$-alkyl)amino-C$_{1-6}$-alkyl-aminocarbonyl, C$_{1-6}$-alkyl-carbonylamino, carbamido, C$_{1-6}$-alkanoyloxy, sulphono, C$_{1-6}$-alkylsulphonyloxy, nitro, azido, sulphanyl, C$_{1-6}$-alkylthio, halogen, where aryl and heteroaryl may be optionally substituted and where two geminal substituents R$^a$ and Rb together may designate optionally substituted methylene (=CH₂), wherein for all chiral centers, asymmetric groups may be found in either R or S orientation.

21. The method according to claim 17, wherein the chiral auxiliary phosphoramidite monomer is of formula 5 or 6,

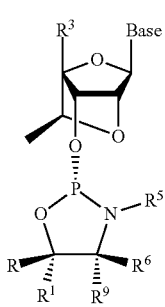

Formula 5

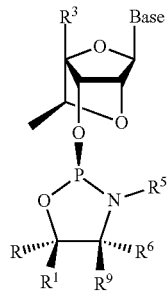

Formula 6 wherein Base is a nucleobase;

R⁵ and R⁶ are independently selected from the group consisting of hydrogen, alkyl, cyclo-alkyl, aryl, heteroaryl, substituted alkyl, substituted cyclo-alkyl, substituted aryl, and substituted heteroaryl, or R⁵ and R⁶ together form a heterocyclic ring comprising 3-16 carbon atoms;

R¹ is selected from the groups consisting of hydrogen and C$_{1-3}$ alkyl; R⁹ is hydrogen;

R is selected from the groups consisting of aryl, heteroaryl, substituted aryl, substituted heteroaryl, nitro, halogen, cyano, silyl, substituted silyl, sulfone, substituted sulfone (aryl substituted sulfone), fluorene, and substituted fluorine;

R³= is selected from the group consisting of CH₂ODMTr, CH₂-Alkyl-O-DMTr, CH-Me-O-DMTr, CH₂OMMTr, CH₂-Alkyl-O-MMTr, CH(Me)-O-MMTr, CH—R$^a$—O-DMTrR$^b$, and CH—R$^a$—O-MMTrR$^b$;

R² is selected from the groups consisting of halo, such as —F, amino, azido, —SH, —CN, —OCN, —CF₃, —OCF₃, —O(R$_m$)-alkyl, —S(R$_m$)-alkyl, —N(R$_m$)-alkyl, —O(R$_m$)-alkenyl, —S(R$_m$)-alkenyl, —N(R$_m$)-alkenyl; —O(R$_m$)-alkynyl, —S(R$_m$)-alkynyl or —N(R$_m$)-alkynyl; O-alkylenyl-O-alkyl, alkynyl, alkaryl, aralkyl, O-alkaryl, O-aralkyl, O(CH₂)₂SCH₃, O—(CH₂)₂—O—N(R$_m$)(R$_n$) or O—CH₂C(=O)—N(R$_m$)(R$_n$), —O—(CH₂)₂OCH₃, and —O—CH₃, where each R$_m$ and R$_n$ are independently, H, an amino protecting group or substituted or unsubstituted C₁-10 alkyl;

R⁴ is selected from the group consisting of alkyl, cyclo-alkyl, cyclo-heteroalkyl, O-alkyl, S-alkyl, NH-alkyl, and hydrogen;

or R² and R⁴ together designate a bivalent bridge consisting of 1, 2, 3 groups/atoms selected from the group consisting of —C(R$^a$R$^b$)—, —C(R$^a$)=C(R$^b$), —C(R$^a$)=N, O, —Si(R$^a$)₂—, S—, —SO₂—, —N(R$^a$)—, and >C=Z;

wherein R$^a$ and, when present R$^b$, each is independently selected from hydrogen, optionally substituted C$_{1-6}$-alkyl, optionally substituted C$_{2-6}$-alkenyl, optionally substituted C$_{2-6}$-alkynyl, hydroxy, optionally substituted C$_{1-6}$-alkoxy, C$_{2-6}$-alkoxyalkyl, C$_{2-6}$-alkenyloxy, carboxy, C$_{1-6}$-alkoxycarbonyl, C$_{1-6}$-alkylcarbonyl, formyl, aryl, aryl-oxy-carbonyl, aryloxy, arylcarbonyl, heteroaryl, hetero-aryloxy-carbonyl, heteroaryloxy, heteroarylcarbonyl, amino, mono- and di(C$_{1-6}$-alkyl)amino, carbamoyl, mono- and di(C$_{1-6}$-alkyl)-aminocarbonyl, amino-C$_{1-6}$-alkyl-aminocarbonyl, mono- and di(C$_{1-6}$-alkyl)amino-C$_{1-6}$-alkyl-aminocarbonyl, C$_{1-6}$-alkyl-carbonylamino, carbamido, C$_{1-6}$-alkanoyloxy, sulphono, C$_{1-6}$-alkylsulphonyloxy, nitro, azido, sulphanyl, C$_{1-6}$-alkylthio, halogen, where aryl and heteroaryl may be optionally substituted and where two geminal substituents $R^a$ and Rb together may designate optionally substituted methylene (=CH$_2$), wherein for all chiral centers, asymmetric groups may be found in either R or S orientation.

22. The method according to claim 17, wherein the chiral auxiliary phosphoramidite monomer is of formula 7 or 8,

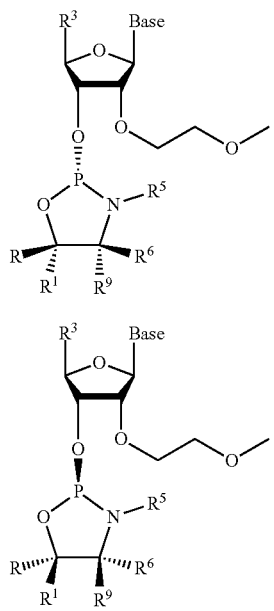

Formula 7

Formula 8 wherein Base is a nucleobase and R, $R^1$, $R^3$, $R^5$, $R^6$ and $R^9$ are as defined in claim 16.

23. The method according to claim 1, wherein the oxazaphospholidine chiral auxiliary phosphoramidite monomer is of Formula 1 or 2:

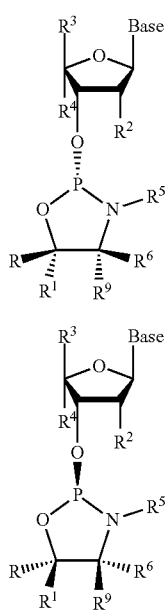

Formula 1

Formula 2 wherein base is a nucleobase;
$R^5$ and $R^6$ are independently selected from the group consisting of hydrogen, alkyl, cyclo-alkyl, aryl, heteroaryl, substituted alkyl, substituted cyclo-alkyl, substituted aryl, and substituted heteroaryl, or $R^5$ and $R^6$ together form a heterocyclic ring comprising 3-16 carbon atoms;
$R^1$ is selected from the groups consisting of hydrogen and $C_{1-3}$ alkyl; $R^9$ is hydrogen;
R is selected from the groups consisting of aryl, heteroaryl, substituted aryl, substituted heteroaryl, nitro, halogen, cyano, silyl, substituted silyl, sulfone, substituted sulfone, (aryl substituted sulfone), fluorene, and substituted fluorine;
$R^3$=is selected from the group consisting of CH$_2$ODMTr, CH$_2$-Alkyl-O-DMTr, CH-Me-O-DMTr, CH$_2$OMMTr, CH$_2$-Alkyl-O-MMTr, CH(Me)-O-MMTr, CH—$R^a$—O-DMTrR$^b$, and CH—$R^a$—O-MMTrR$^b$;
$R^2$ is selected from the groups consisting of hydrogen, halo, such as —F, amino, azido, —SH, —CN, —OCN, —CF$_3$, —OCF$_3$, —O(R$_m$)-alkyl, —S(R$_m$)-alkyl, —N(R$_m$)-alkyl, —O(R$_m$)-alkenyl, —S(R$_m$)-alkenyl, —N(R$_m$)-alkenyl; —O(R$_m$)-alkynyl, —S(R$_m$)-alkynyl or —N(R$_m$)-alkynyl; O-alkylenyl-O-alkyl, alkynyl, alkaryl, aralkyl, O-alkaryl, O-aralkyl, O(CH$_2$)$_2$SCH$_3$, O—(CH$_2$)$_2$—O—N(R$_m$)(R$_n$) or O—CH$_2$C(=O)—N(R$_m$)(R$_n$), —O—(CH$_2$)$_2$OCH$_3$, and —O—CH$_3$, where each $R_m$ and $R_n$ are independently, H, an amino protecting group or substituted or unsubstituted $C_{1-10}$ alkyl;
$R^4$ is selected from the group consisting of alkyl, cycloalkyl, cyclo-heteroalkyl, O-alkyl, S-alkyl, NH-alkyl, and hydrogen;
or $R^2$ and $R^4$ together designate a bivalent bridge consisting of 1, 2, 3 groups/atoms selected from the group consisting of —C($R^aR^b$)—, —C($R^a$)=C($R^b$), —C($R^a$)=N, O, —Si($R^a$)$_2$—, S—, —SO$_2$—, —N($R^a$)—, and >C=Z;
wherein $R^a$ and, when present $R^b$, each is independently selected from hydrogen, optionally substituted $C_{1-6}$-alkyl, optionally substituted $C_{2-6}$-alkenyl, optionally substituted $C_{2-6}$-alkynyl, hydroxy, optionally substituted $C_{1-6}$-alkoxy, $C_{2-6}$-alkoxyalkyl, $C_{2-6}$-alkenyloxy, carboxy, $C_{1-6}$-alkoxycarbonyl, $C_{1-6}$-alkylcarbonyl, formyl, aryl, aryl-oxy-carbonyl, aryloxy, arylcarbonyl, heteroaryl, hetero-aryloxy-carbonyl, heteroaryloxy, heteroarylcarbonyl, amino, mono- and di($C_{1-6}$-alkyl) amino, carbamoyl, mono- and di($C_{1-6}$-alkyl)-aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, where aryl and heteroaryl may be optionally substituted and where two geminal substituents $R^a$ and Rb together may designate optionally substituted methylene (=CH$_2$), wherein for all chiral centers, asymmetric groups may be found in either R or S orientation.

24. The method according to claim 1, wherein the coupling step (i) takes place in an acetonitrile solvent composition comprising acetonitrile and an aromatic heterocyclic solvent, and optionally an activator.

25. The method according to claim 24, wherein the aromatic heterocyclic solvent has a pKa of 4-7 or from 7-17 in water at 20° C.

26. The method according to claim 24, wherein the aromatic heterocyclic solvent is an aromatic heterocyclic base.

27. The method according claim 24, wherein the aromatic heterocyclic solvent is an aromatic heterocyclic acid.

28. The method according to claim 24, wherein the aromatic heterocyclic solvent is selected from the group consisting of pyridine, 2-picoline, 4-picoline, 3-picoline, lutidine, and pyrrole.

29. The method according to claim 24, wherein the concentration (v/v), of aromatic heterocyclic solvent in acetonitrile is between about 0.1% and about 50% (v/v).

30. The method according to claim 24, wherein the concentration (v/v), of aromatic heterocyclic solvent in acetonitrile is between about 0.5% and about 10%.

31. The method according to claim 24, wherein the activator comprises N-methylimidazole.

32. The method according to claim 24, wherein the activator comprises 4,5-dicyanoimidazole (DCI), tetrazole, or 5-(Benzylthio)-1H-tetrazole.

33. The method according to claim 24, wherein the solvent composition comprises about 0.5-about 2M DCI.

34. The method according to claim 24, wherein the solvent composition comprises N-methylimidazole in a concentration of 0.01-about 1M N-methylimidazole.

35. The method according to claim 1, wherein method comprises at least 2 synthesis cycles which each comprise the coupling, sulfurization and protection steps, (i), (ii), and (iii).

36. The method according to claim 1, wherein the oligonucleotide synthesized by the method is an LNA oligonucleotide.

37. The method according to claim 36, wherein the 3' most nucleoside is an LNA nucleoside.

38. The method according to claim 37, wherein the step of global deprotection and cleavage from solid support is performed in a period of less than 8 hours.

39. The method according to claim 1, wherein the method comprises the following steps:
  a) Provision of a solid support comprising a blocked terminal —OH group either attached to the solid support or a preceding nucleoside attached to the solid support (a terminal 5' —OH group)
  b) Unblocking of the terminal —OH group
  c) Performing the method of any one of the preceding claims
  d) Optionally repeating steps a)-c) for one or more further cycles (chain elongation)
  e) Removal of the carbamate protection group,
  f) Removal of the chiral auxiliary group(s)
  g) Cleavage of the oligonucleotide from the solid support, wherein steps e), f) and g) are performed either sequentially or simultaneously, or step e) is performed prior to the step of removal of the chiral auxiliary and cleavage from the solid support.

* * * * *